United States Patent
Iwahori

(10) Patent No.: US 8,863,343 B2
(45) Date of Patent: Oct. 21, 2014

(54) ORAL CARE APPARATUS

(75) Inventor: Toshiyuki Iwahori, Mishima-gun (JP)

(73) Assignee: Omron Healthcare Co., Ltd., Muko-shi (JP)

( * ) Notice: Subject to any disclaimer, the term of this patent is extended or adjusted under 35 U.S.C. 154(b) by 0 days.

(21) Appl. No.: 13/491,032

(22) Filed: Jun. 7, 2012

(65) Prior Publication Data

US 2012/0251975 A1   Oct. 4, 2012

Related U.S. Application Data

(63) Continuation of application No. PCT/JP2011/051095, filed on Jan. 21, 2011.

(30) Foreign Application Priority Data

Feb. 2, 2010   (JP) ................................. 2010-021097

(51) Int. Cl.
*A61C 17/22*   (2006.01)
*A61C 17/34*   (2006.01)

(52) U.S. Cl.
CPC ................................. *A61C 17/3481* (2013.01)
USPC ......................................................... 15/22.1

(58) Field of Classification Search
CPC ........ A61C 17/22; A61C 1/07; A61C 17/221; A61C 17/3481; A46B 15/0006; A46B 15/0002; A46B 15/0012; A46B 15/0038; A46B 13/023
USPC .......................................... 15/22.1; 433/119
See application file for complete search history.

(56) References Cited

U.S. PATENT DOCUMENTS

| | | | | | |
|---|---|---|---|---|---|
| 1,803,458 | A | * | 5/1931 | Berry ............................... | 74/63 |
| 3,685,080 | A | * | 8/1972 | Hubner .......................... | 15/22.1 |
| 4,591,748 | A | * | 5/1986 | Greer .............................. | 310/81 |
| 4,716,614 | A | * | 1/1988 | Jones et al. ..................... | 15/105 |
| 4,940,336 | A | * | 7/1990 | Dryga et al. ................... | 366/128 |
| 5,214,819 | A | * | 6/1993 | Kirchner ........................ | 15/22.1 |
| 5,493,747 | A | * | 2/1996 | Inakagata et al. .............. | 15/22.1 |
| 5,561,881 | A | * | 10/1996 | Klinger et al. ................. | 15/22.1 |
| 5,651,157 | A | * | 7/1997 | Hahn ............................. | 15/22.1 |
| 5,749,381 | A | * | 5/1998 | Butler et al. ................... | 132/309 |

(Continued)

FOREIGN PATENT DOCUMENTS

| | | | | | |
|---|---|---|---|---|---|
| GB | 2466472 | A | * | 6/2010 | ............. G01R 31/34 |
| JP | 63140963 | A | * | 6/1988 | ................ G01P 3/14 |

(Continued)

OTHER PUBLICATIONS

International Search Report issued in International Patent Application No. PCT/JP2011/051095 dated May 10, 2011.

(Continued)

*Primary Examiner* — Lee D Wilson
*Assistant Examiner* — Marc Carlson
(74) *Attorney, Agent, or Firm* — Oliff PLC

(57) ABSTRACT

An oral care apparatus is an apparatus for performing care on an oral cavity using a care member, and includes an accelerometer, a driving unit for vibrating the care member, and a vibration frequency detection unit for detecting a vibration frequency of the care member. The vibration frequency detection unit detects the vibration frequency based on the waveform of a signal outputted by the accelerometer.

6 Claims, 28 Drawing Sheets

(56) References Cited

U.S. PATENT DOCUMENTS

| | | | |
|---|---|---|---|
| 5,850,659 A * | 12/1998 | Butler et al. | 15/167.1 |
| 5,987,681 A * | 11/1999 | Hahn et al. | 15/22.1 |
| 6,536,068 B1 * | 3/2003 | Yang et al. | 15/105 |
| 6,564,940 B2 * | 5/2003 | Blaustein et al. | 206/362.2 |
| 6,611,780 B2 * | 8/2003 | Lundell et al. | 702/122 |
| 6,739,012 B2 * | 5/2004 | Grez et al. | 15/22.1 |
| 6,766,548 B1 * | 7/2004 | Lukas et al. | 15/22.1 |
| 7,310,844 B1 * | 12/2007 | Rehkemper | 15/22.1 |
| 7,464,430 B2 * | 12/2008 | Filsouf | 15/22.1 |
| 8,032,965 B2 * | 10/2011 | Asada et al. | 15/22.1 |
| 8,272,091 B2 * | 9/2012 | Hwang et al. | 15/22.1 |
| 8,341,791 B2 * | 1/2013 | Iwahori | 15/22.1 |
| 2002/0133308 A1 * | 9/2002 | Lundell et al. | 702/122 |
| 2002/0183959 A1 * | 12/2002 | Savill et al. | 702/150 |
| 2003/0115693 A1 * | 6/2003 | Grez et al. | 15/22.1 |
| 2003/0158758 A1 * | 8/2003 | Kanazawa et al. | 705/4 |
| 2007/0083209 A1 * | 4/2007 | Schenberger et al. | 606/82 |
| 2007/0190509 A1 * | 8/2007 | Kim | 434/263 |
| 2007/0294847 A1 * | 12/2007 | Wang | 15/22.2 |
| 2008/0022469 A1 * | 1/2008 | Hilscher et al. | 15/22.1 |
| 2008/0060148 A1 * | 3/2008 | Pinyayev et al. | 15/22.1 |
| 2009/0025156 A1 * | 1/2009 | Asada et al. | 15/22.1 |
| 2009/0070947 A1 * | 3/2009 | Baertschi et al. | 15/22.1 |
| 2009/0092955 A1 * | 4/2009 | Hwang | 434/263 |
| 2009/0130636 A1 * | 5/2009 | Hwang | 433/216 |
| 2009/0143914 A1 * | 6/2009 | Cook et al. | 700/275 |
| 2009/0188058 A1 * | 7/2009 | Schwarz-Hartmann et al. | 15/22.2 |
| 2010/0106336 A1 * | 4/2010 | Hwang et al. | 700/280 |
| 2011/0005015 A1 * | 1/2011 | Iwahori et al. | 15/22.1 |
| 2011/0010875 A1 * | 1/2011 | Iwahori et al. | 15/22.1 |
| 2011/0010876 A1 * | 1/2011 | Iwahori et al. | 15/22.1 |
| 2011/0041268 A1 * | 2/2011 | Iwahori et al. | 15/22.1 |
| 2011/0041269 A1 * | 2/2011 | Iwahori | 15/22.1 |
| 2011/0256496 A1 * | 10/2011 | Arzanpour | 433/27 |
| 2012/0036657 A1 * | 2/2012 | Iwahori et al. | 15/22.1 |
| 2012/0266397 A1 * | 10/2012 | Iwahori | 15/22.1 |

FOREIGN PATENT DOCUMENTS

| | | | | |
|---|---|---|---|---|
| JP | A-10-108734 | | 4/1998 | |
| JP | A-2005-152217 | | 6/2005 | |
| JP | A-2008-543418 | | 12/2008 | |
| JP | A-2009-240759 | | 10/2009 | |
| JP | A-2009-285416 | | 12/2009 | |
| JP | A-2010-213908 | | 9/2010 | |
| WO | WO 2006/137648 | * | 12/2006 | A61C 17/22 |
| WO | WO 2006/137648 A1 | | 12/2006 | |
| WO | WO 2009/113491 A1 | | 9/2009 | |
| WO | WO 2009/148018 A1 | | 12/2009 | |
| WO | WO 2010/106850 A1 | | 9/2010 | |

OTHER PUBLICATIONS

Jan. 21, 2014 Office Action issued in Japanese Application 2010-021097 (with English Translation).

* cited by examiner

MAXILLA

FIG. 10

| AREA | BRUSHING TIME (SEC) | BRUSH ANGLE (DEG) | BRUSH PRESSURE (g) | BRUSHING INDEX |
|---|---|---|---|---|
| MAXILLARY ANTERIOR BUCCAL SIDE | 7.5 | 70 | 120 | 78 |
| MAXILLARY ANTERIOR LINGUAL SIDE | — | — | — | — |
| MAXILLARY LEFT BUCCAL SIDE | 12.2 | 45 | 108 | 100 |
| MAXILLARY LEFT LINGUAL SIDE | — | — | — | — |
| MAXILLARY RIGHT BUCCAL SIDE | — | — | — | — |
| MAXILLARY RIGHT LINGUAL SIDE | — | — | — | — |
| MANDIBULAR ANTERIOR BUCCAL SIDE | — | — | — | — |
| MANDIBULAR ANTERIOR LINGUAL SIDE | — | — | — | — |
| MANDIBULAR LEFT BUCCAL SIDE | 2.0 | 53 | 95 | 25 |
| MANDIBULAR LEFT LINGUAL SIDE | — | — | — | — |
| MANDIBULAR RIGHT BUCCAL SIDE | — | — | — | — |
| MANDIBULAR RIGHT LINGUAL SIDE | — | — | — | — |

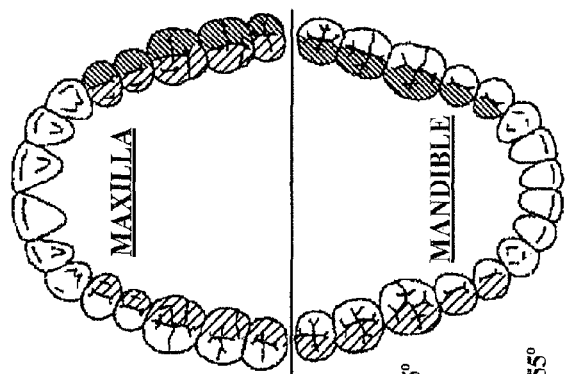

BRUSH ANGLE

EXAMPLE OF AREA-BY-AREA EVALUATION

MAXILLARY LEFT BUCCAL SIDE: MORE THAN 55°
MAXILLARY LEFT LINGUAL SIDE: 35 TO 55°
MAXILLARY ANTERIOR BUCCAL SIDE: MORE THAN 55°
MAXILLARY ANTERIOR LINGUAL SIDE: MORE THAN 55°
MAXILLARY RIGHT BUCCAL SIDE: LESS THAN 35°
MAXILLARY RIGHT LINGUAL SIDE: 35 TO 55°
MANDIBULAR LEFT BUCCAL SIDE: 35 TO 55°
MANDIBULAR LEFT LINGUAL SIDE: MORE THAN 55°
MANDIBULAR ANTERIOR BUCCAL SIDE: MORE THAN 55°
MANDIBULAR ANTERIOR LINGUAL SIDE: MORE THAN 55°
MANDIBULAR RIGHT BUCCAL SIDE: MORE THAN 55°
MANDIBULAR RIGHT LINGUAL SIDE: LESS THAN 35°

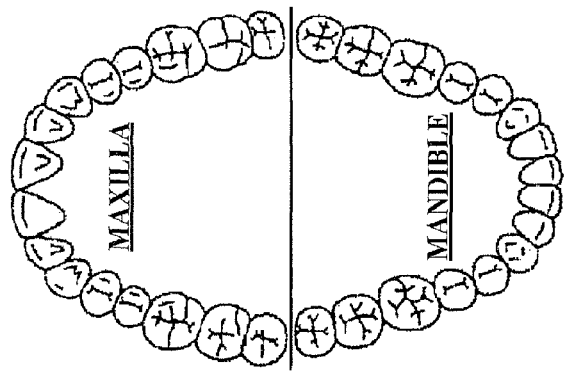

: LESS THAN 35°
: 35° TO 55°
: MORE THAN 55°

INITIAL STATE

BRUSHING EVALUATION DISPLAY EXAMPLE

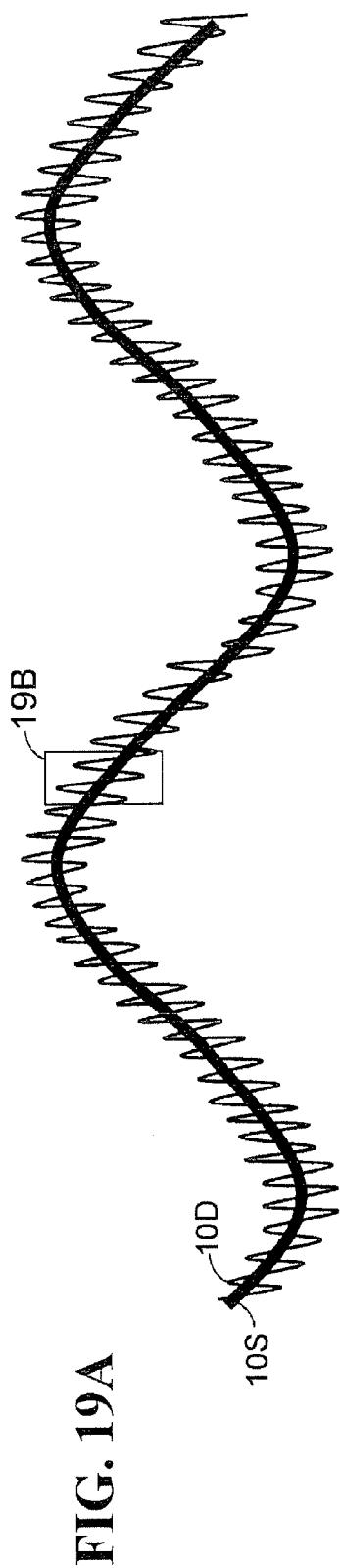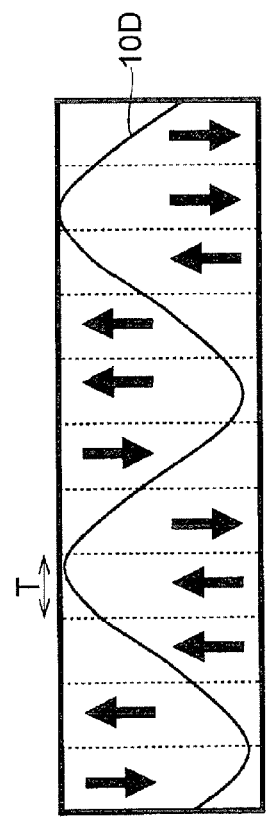
FIG. 19A
FIG. 19B

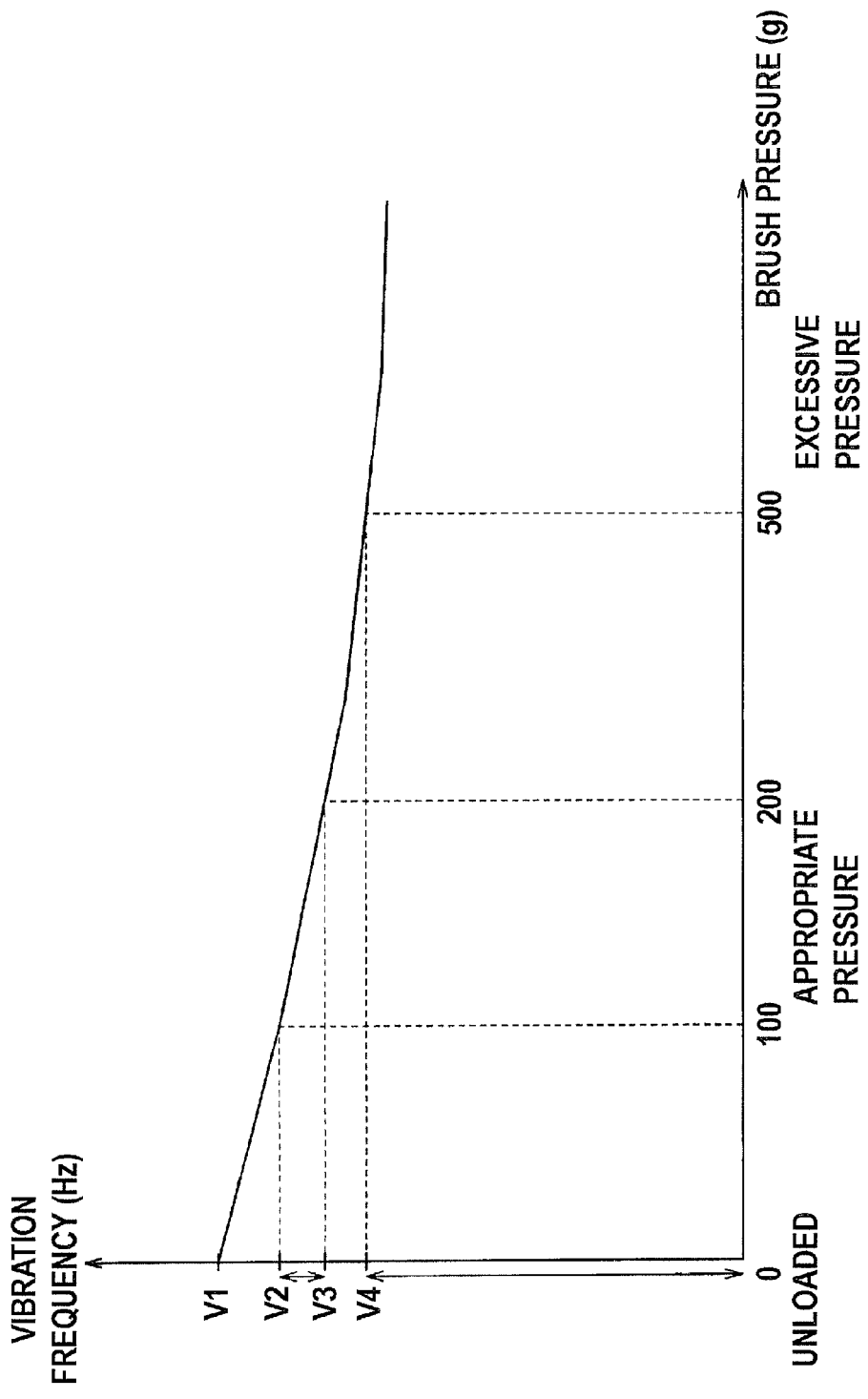

| MD MODE | BV BATTERY VOLTAGE | 2.4V | 2.2V | 2V |
|---|---|---|---|---|
| HIGH | | 80% | 88% | 96% |
| MEDIUM | | 60% | 66% | 72% |
| LOW | | 40% | 44% | 48% |

| MD : MODE | BV | | |
|---|---|---|---|
| | 2.4V | 2.2V | 2V |
| HIGH | (UNLOADED) 300Hz | 290Hz | 280Hz |
| MEDIUM | 200Hz | 195Hz | 190Hz |
| LOW | 100Hz | 98Hz | 96Hz |

TB4

DV

ORAL CARE APPARATUS

This is a Continuation of International Application No. PCT/JP2011/051095 filed on Jan. 21, 2011, which claims the benefit of Japanese Patent Application No. 2010-021097filed Feb. 2, 2010. The disclosures of the prior applications are hereby incorporated by reference herein in their entirety.

TECHNICAL FIELD

This invention relates to oral care apparatuses, and particularly relates to an oral care apparatus that has a function for detecting a vibration frequency using an accelerometer.

BACKGROUND ART

An electric toothbrush is one example of an oral care apparatus. It is known that in order to effectively remove plaque when brushing using an electric toothbrush, it is important to control the load acting on the brush (called "brush pressure" hereinafter) when, for example, the brush is making contact with the teeth.

Electric toothbrushes are typically capable of detecting the brush pressure on the teeth based on the current consumed by a motor (Patent Citation 1 (JP-2005-152217A). As another method, the brush pressure can be detected using a strain gauge (Patent Citation 2 (JP-H10-108734A).

CITATION LIST

Patent Literature

Patent Citation 1: JP-2005-152217A
Patent Citation 2: JP-H10-108734A

SUMMARY OF INVENTION

Technical Problem

With the stated method that detects the current consumed by a motor, the motor produces heat as the operating time of the motor increases, which causes the current consumed to fluctuate even if the motor is operating at a constant vibration frequency; thus the detection accuracy of this method has been insufficient.

Meanwhile, with the method that uses a strain gauge, the strain gauge cannot take accurate measurements if the angle at which the brush is tilted relative to the teeth changes. In addition, it is necessary to dispose the strain gauge in the brush head, and there has thus been a risk of the wires for the strain gauge being cut due to the vibration of the electric toothbrush. Furthermore, with an electric toothbrush that has a replaceable brush, there is a risk of poor connections between the wires or moisture infiltrating at the connection point between the brush and the main body, and it has thus been necessary to make structural improvements to prevent this from occurring.

In light of this, it is an object of this invention to provide an oral care apparatus capable of obtaining a reference value (a base value) for estimating a load acting on an oral care member, using a simple configuration.

Solution to Problem

An oral care apparatus according to an aspect of this invention is an apparatus for performing care on an oral cavity using a care member, and includes an accelerometer, a driving unit for vibrating the care member, and a vibration frequency detection unit for detecting a vibration frequency of the care member. The vibration frequency detection unit detects the vibration frequency based on the waveform of a signal outputted by the accelerometer.

Preferably, the oral care apparatus detects a member pressure indicating a load acting on the care member based on the vibration frequency detected by the vibration frequency detection unit.

Preferably, the driving unit is a motor, and the vibration frequency detection unit detects the member pressure based on a difference between the vibration frequency caused by rotation of the motor when the motor is unloaded and the vibration frequency detected by the vibration frequency detection unit.

Preferably, the driving unit is a motor, and the oral care apparatus further includes a consumed current detection unit that detects the current consumed by the motor. The vibration frequency detection unit further detects the vibration frequency based on the consumed current detected by the consumed current detection unit.

Preferably, the oral care apparatus further includes a power source that supplies power to the respective elements of the oral care apparatus, a power detection unit that detects the power outputted by the power source, and a power compensation unit that supplements the power supplied to the driving unit based on the value of the power detected by the power detection unit.

Preferably, the power compensation unit changes the duty ratio of a pulse signal supplied to the driving unit for driving based on the value of the power detected by the power detection unit.

Preferably, the oral care apparatus communicates the detected member pressure.

Preferably, the oral care apparatus displays the detected vibration frequency.

Advantageous Effects of Invention

According to the present invention, it is possible to obtain a vibration frequency serving as a reference value (a base value) for estimating a member pressure acting on an oral care member, using a simple configuration employing an accelerometer.

BRIEF DESCRIPTION OF DRAWINGS

FIG. 10 is a diagram illustrating an example of brushing information.

FIG. 14 is a diagram illustrating an example of the output of a brush angle serving as a brushing result.

FIG. 19 is a diagram illustrating an output waveform of a filter unit.

FIG. 20 is a diagram illustrating a correlation relationship between the vibration frequency of a motor and a load.

FIG. 28 is a diagram illustrating an example of a table referred to in order to find a brush pressure.

DESCRIPTION OF EMBODIMENTS

Figure 1:
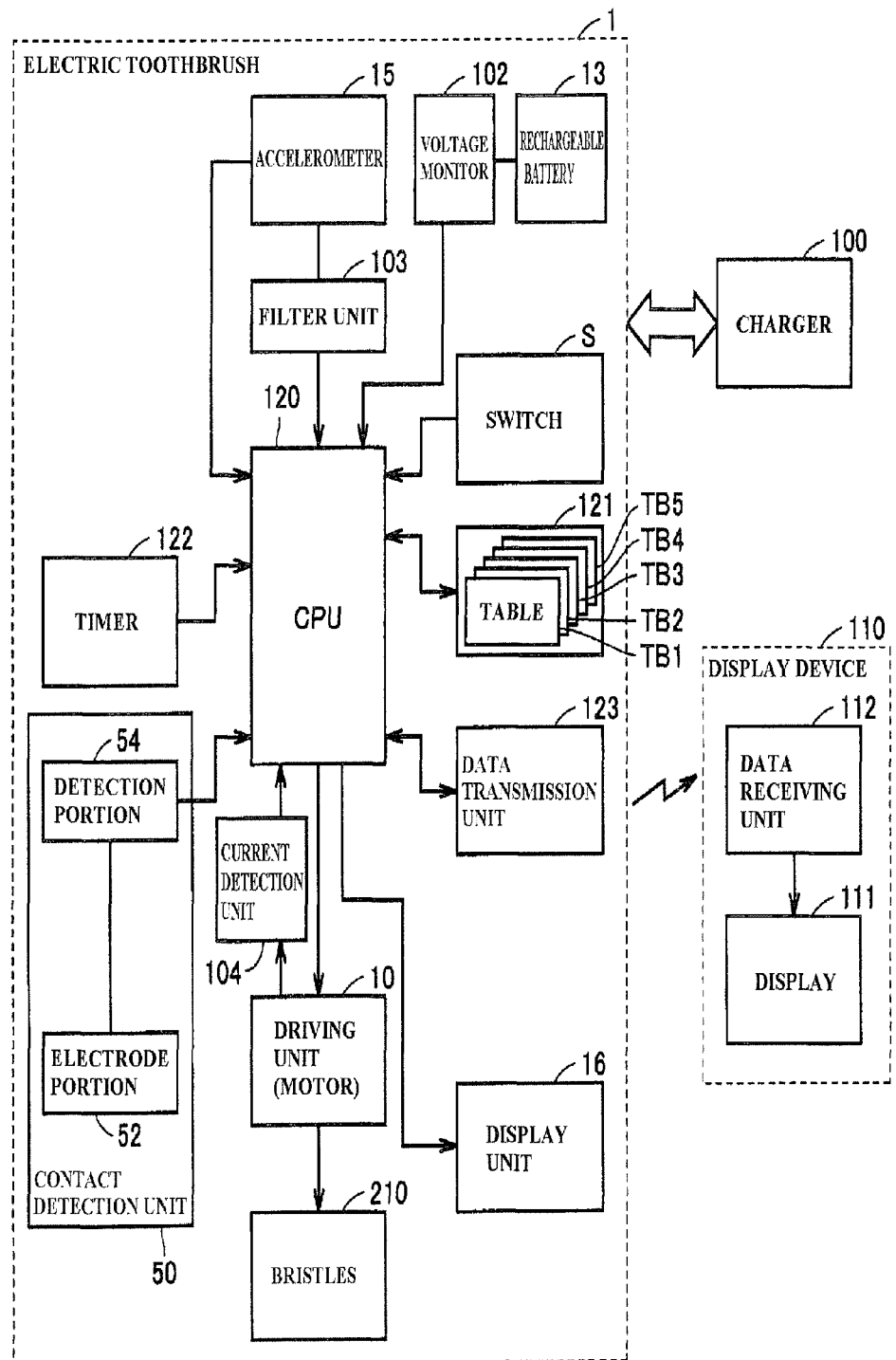
FIG. 1 is a block diagram illustrating a display system including an electric toothbrush according to an embodiment.

An embodiment of the present invention will be described hereinafter with reference to the drawings. Note that identical or corresponding areas of the drawings will be assigned the same reference numerals, and descriptions thereof will not be repeated.

Although the embodiment describes an electric toothbrush having bristles implanted in the surface of a housing as an example of an oral care apparatus, the configuration of the embodiment can be applied generally in apparatuses capable of being used in oral care (cleaning teeth, brushing, gum massaging, or the like). Specifically, the embodiment can be applied in an apparatus that employs, as a material used in oral care, a resinous component such as a sponge, rubber, an elastomer, or the like in place of a toothbrush, or an oral care member in which such a resinous component is combined with bristles. In such an oral care apparatus, the aforementioned brush pressure corresponds to a "member pressure" indicating a load acting on the care member.

Configuration

The configuration of an electric toothbrush will be described with reference to FIGS. 1 through 3.

Figure 2:
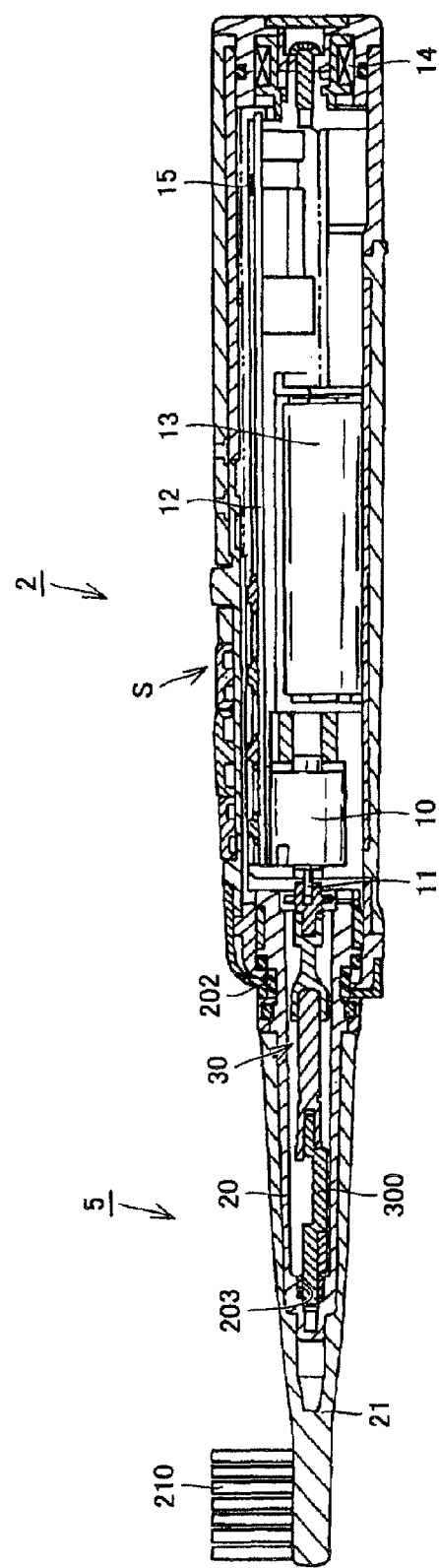
FIG. 2 is a cross-sectional view illustrating an example of the internal configuration of the electric toothbrush according to the embodiment.

FIG. 1 is a block diagram illustrating a display system including the electric toothbrush; FIG. 2 is a cross-sectional view illustrating an example of the internal configuration of the electric toothbrush; and FIG. 3 is a perspective view illustrating an example of the external appearance of the display system including the electric toothbrush.

An electric toothbrush 1 includes a main body portion 2 (also called simply a "main body 2" hereinafter) that includes a motor 10 serving as a driving source, and a vibrating member 5 that vibrates as a result of the driving of the motor 10. Accordingly, the vibrating member 5 is taken as the electric toothbrush main body, and the rotational frequency of the motor 10 corresponds to the vibration frequency of the electric toothbrush main body. The main body 2 has an overall cylindrical shape, and also functions as a handle portion that a user grips with his/her hand when brushing his/her teeth.

Furthermore, the electric toothbrush 1 according to the present embodiment includes a charger 100, on which the main body 2 is placed and that charges the electric toothbrush 1, and a display device 110 for outputting a brushing result.

A switch S for turning the power on and off and for switching between operating modes of the motor 10, mentioned later, is provided in the main body 2. Meanwhile, the motor 10 (for example, a DC motor) serving as a driving source, a driving circuit 12, a rechargeable battery 13 serving as a power source with an output rating of 2.4 V for supplying power to the various constituent elements, a charging coil 14, and so on are provided within the main body 2. When charging the rechargeable battery 13, non-contact charging can be carried out through electromagnetic induction simply by placing the main body 2 on the charger 100. The driving circuit 12 includes a CPU (Central Processing Unit) 120 that executes various types of computations and control, a memory 121 that stores programs, various types of configuration values, and tables TB1 through TB5 (mentioned later) in advance, a timer 122, a data transmission unit 123, and so on. The data transmission unit 123 carries out wireless communication with a data receiving unit 112 of the display device 110. The display device 110 includes a display 111 for outputting data such as brushing results received by the data receiving unit 112.

A voltage monitor 102 for detecting the output voltage (remaining charge) of the rechargeable battery 13, a filter unit 103 for filtering output signals from an accelerometer 15, and a current detection unit 104 for detecting a current supplied to the motor 10 (in other words, the current consumed by the motor 10) are furthermore provided.

In addition, the main body 2 further includes an integrated display unit 16 for displaying brushing results.

Figure 3:
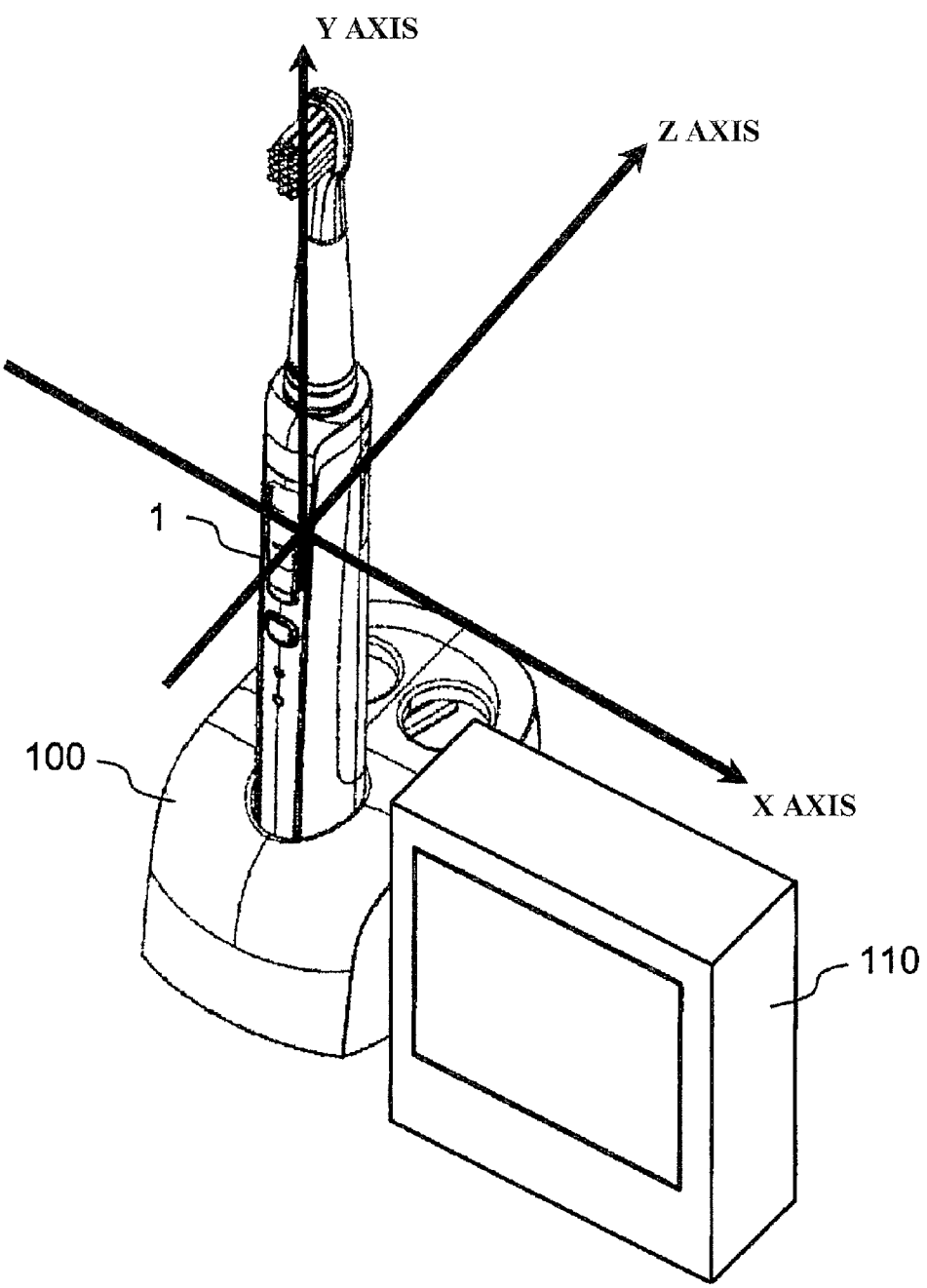
FIG. 3 is a perspective view illustrating an example of the external appearance of the display system including the electric toothbrush according to the embodiment.

FIG. 3 illustrates the external appearance of the electric toothbrush 1 when mounted on the charger 100, along with the display device 110.

The multi-axis (here, three axes, or x, y, and z axes) accelerometer 15, for example, is provided within the main body 2 in order to detect the orientation of the electric toothbrush 1. As shown in FIG. 3, the accelerometer 15 is installed so that the x axis is parallel to a brush surface, the y axis matches the lengthwise direction of the main body 2, and the z axis is perpendicular to the brush surface. In other words, when the main body 2 has been placed on the charger 100, the gravity acceleration vector is parallel to the y axis; when the brush surface is pointed upward, the gravity acceleration vector is parallel to the z axis; and when the main body 2 is placed horizontally and the brush surface is pointed sideways, the gravity acceleration vector is parallel to the x axis. The outputs of the axes of the accelerometer 15 are inputted into the CPU 120, and are used to detect a three-dimensional orientation of the brush.

A piezoelectric resistance-type, an electrostatic capacitance-type, or a thermal detection-type micro electro mechanical systems (MEMS) sensor can be used favorably as the accelerometer 15. MEMS sensors are extremely small and can therefore easily be incorporated into the main body 2. However, the type of the accelerometer 15 is not limited thereto, and an electrokinetic sensor, a strain gauge sensor, a piezoelectric sensor, or the like may be used instead. In addition, although not particularly shown, it is beneficial to provide correction circuits for correcting the balance of sensitivities, temperature characteristics of the sensitivities, temperature drift, and so on of the sensors in the respective axes. Furthermore, a band pass filter (low-pass filter) for removing dynamic acceleration components, noise, and so on may be provided. Further still, noise may be reduced by smoothing the waveforms of the outputs from the accelerometer.

The vibrating member 5 includes a stem portion 20 that is anchored to the main body 2 and a brush component 21 that is mounted to the stem portion 20. Bristles 210 are implanted in the tip of the brush component 21. The brush component 21 is a consumable item, and is thus configured so as to be removable from the stem portion 20 for replacement.

The brush component 21 of the vibrating member 5 includes a brush portion in which the bristles 210 are disposed and a shank portion located toward the main body 2. Although the present embodiment illustrates a configuration in which the brush component 21 that includes the comparatively long shank portion can be replaced, it should be noted that the configuration may be such that only the brush portion, or a brush component that includes the brush portion and a short shank portion, can be replaced. In other words, the configuration may be such that part or all of the shank portion is included as part of the main body.

The stem portion 20 is configured of a resin material. The stem portion 20 is attached to the main body 2 via an elastic member 202 configured of an elastomer. The stem portion 20 is a closed-ended (on the brush-side end) cylindrical member, and has a shaft bearing 203 at a distal end within the cylinder. The distal end of an eccentric shaft 30 that is linked to a rotating shaft 11 of the motor 10 is inserted into the shaft bearing 203 of the stem portion 20. This eccentric shaft 30 has a weight 300 in the vicinity of the shaft bearing 203, and thus the center of gravity of the eccentric shaft 30 is offset from the rotational center thereof. Note that a minute clearance is provided between the distal end of the eccentric shaft 30 and the shaft bearing 203.

The electric toothbrush 1 further includes an electrode-based contact detection unit 50 for detecting contact or proximity. The contact detection unit 50 detects contact with or proximity to a body, or in other words, the cheek mucosa and the tongue, during brushing. Specifically, the contact detection unit 50 includes an electrode portion 52 and a detection portion 54 for detecting an impedance from the electrode portion 52. The detection portion 54, meanwhile, may be installed within the driving circuit 12. The detection portion 54 within the driving circuit 12 is capable of detecting an impedance by detecting a current that flows through the electric circuit configured by the electrode portion 52. Contact with or proximity to the cheek mucosa and the tongue is detected based on the impedance value.

Principles of Driving Electric Toothbrush

The CPU 120 supplies a driving signal (for example, a PWM (pulse width modulation) signal) to the motor 10 in accordance with an operating mode, thus causing the rotating shaft 11 of the motor 10 to rotate. The eccentric shaft 30 also rotates due to the rotation of the rotating shaft 11, but because the center of gravity of the eccentric shaft 30 is offset, the eccentric shaft 30 moves in gyrations central to the rotational center. Accordingly, the distal end of the eccentric shaft 30 repeatedly collides with the inner wall of the shaft bearing 203, which causes the stem portion 20 and the brush component 21 attached thereto to vibrate (move) at a high rate of speed. In other words, the motor 10 serves as a driving unit that causes the brush to vibrate (move), and the eccentric shaft 30 serves as a motion transmission mechanism (motion conversion mechanism) that converts the output of the motor 10 (that is, rotation) into vibration of the vibrating member 5.

The user can brush his or her teeth by gripping the main body 2 in his or her hand and pressing the bristles 210, which are vibrating at a high rate of speed, against his or her teeth. Note that the CPU 120 monitors the continuous operating time using the timer 122, and automatically stops the vibration of the brush after a predetermined amount of time (for example, two minutes) has passed.

With the electric toothbrush 1 according to the present embodiment, the eccentric shaft 30, which serves as the motion transmission mechanism, is contained within the vibrating member 5, and the weight 300 in particular is disposed in the vicinity of the bristles 210. Therefore, the portion that includes the bristles 210 can be caused to vibrate in an efficient manner. Meanwhile, the vibrating member 5 (the stem portion 20) is attached to the main body 2 via the elastic member 202, and thus the vibration of the vibrating member 5 is not easily transmitted to the main body 2. This makes it possible to reduce vibrations in the main body 2 and in the hand when brushing the teeth, which makes it possible to improve the comfort of use.

Operations of Electric Toothbrush

The manner in which food residue, plaque, and so on adheres to a tooth depends on the type of the tooth (in the maxilla/mandible, whether a molar/incisor, and so on), and the area of the tooth (the lingual side/buccal side, the side surface/occlusal surface of the tooth, and so on). Accordingly, effective brushing operations, such as the way in which the brush is applied (the brush angle, brush pressure, and so on), the way the brush is moved, the speed, the brushing time, and so on differ for different areas of the dentition. In light of this, it is desirable to evaluate whether or not proper brushing is being carried out on an area-by-area basis.

Accordingly, the electric toothbrush 1 according to the present embodiment evaluates brushing on an area-by-area basis by accurately estimating a brushing area based on the orientation of the brush as detected by the accelerometer 15 (orientation information) and detection results from the contact detection unit 50. Various items for evaluation are conceivable, but here, three items, or the brushing time, brush angle, and brush pressure, will be described as being evaluated.

In the present embodiment, the upper dentition and lower dentition are segmented into 12 areas: a maxillary anterior buccal side; a maxillary anterior lingual side; a maxillary left buccal side; a maxillary left lingual side; a maxillary right buccal side; a maxillary right lingual side; a mandibular anterior buccal side; a mandibular anterior lingual side; a mandibular left buccal side; a mandibular left lingual side; a mandibular right buccal side; and a mandibular right lingual side. However, the segmentation of the dentition is not limited thereto, and broader or narrower segmentation may be carried out instead. For example, the upper and lower left and right occlusal surfaces may be taken into consideration as well.

Note that because the tongue is not present in the maxilla, the maxillary anterior lingual side, maxillary left lingual side, and maxillary right lingual side are given the more precise names of "maxillary anterior palatal side", "maxillary left palatal side", and "maxillary right palatal side", respectively. Likewise, because the cheeks are not present in the anterior jaw area, the maxillary anterior buccal side and the mandibular anterior buccal side are given the more precise names of "maxillary anterior labial side" and "mandibular anterior labial side", respectively.

Figure 4:
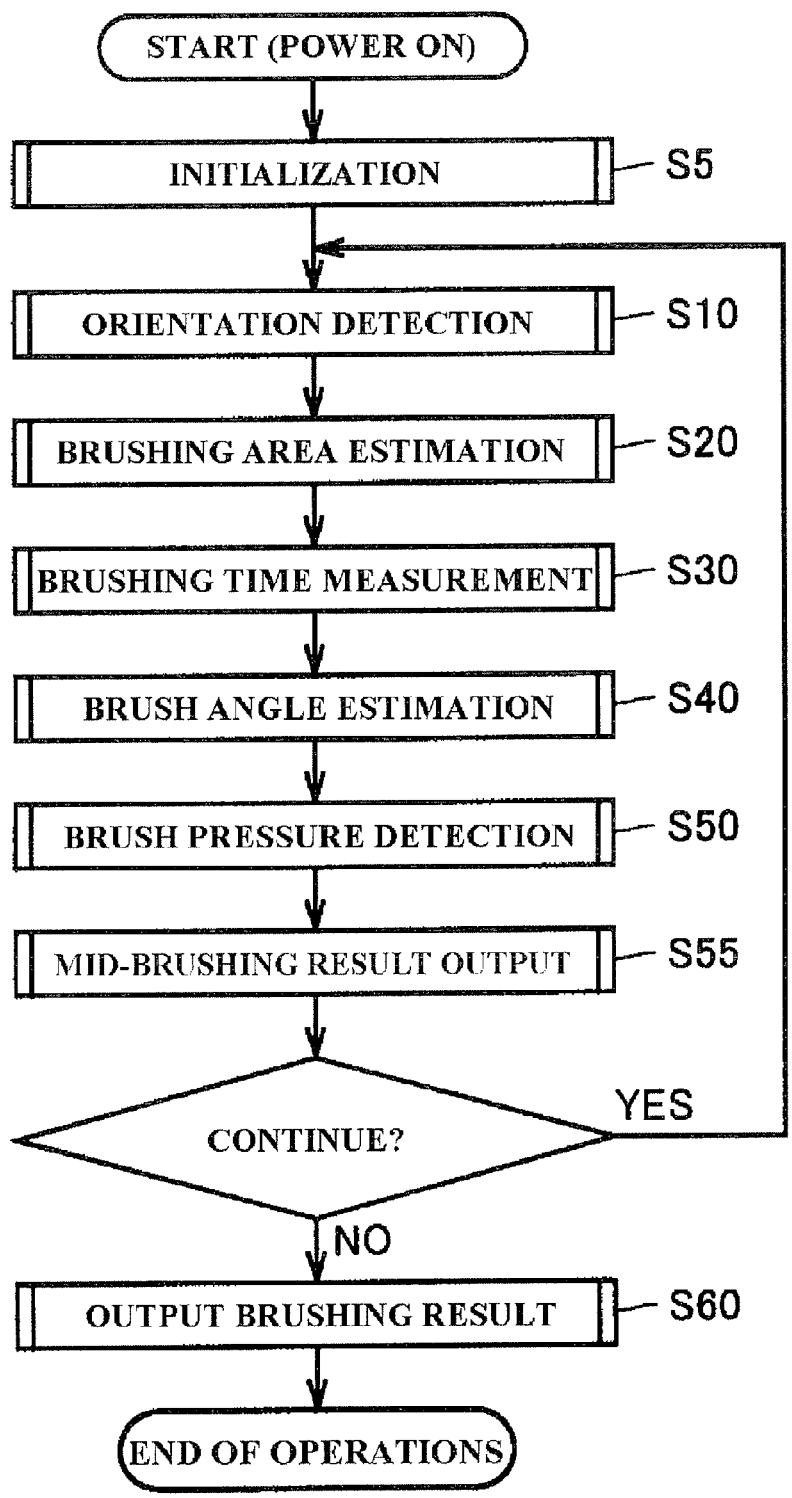
FIG. 4 is a flowchart illustrating a brushing evaluation process according to the embodiment.

A flow of the brushing evaluation will be described in detail with reference to the flowcharts shown in FIGS. 4 through 7. FIG. 4 is a flowchart illustrating a main routine, whereas FIGS. 5 through 7 and 21 are flowcharts illustrating various processes in the main routine in detail. Note that unless explicitly mentioned otherwise, the processes described hereinafter are executed by the CPU 120 in accordance with programs stored in the memory 121.

When the electric toothbrush 1 is turned on, the CPU 120 carries out an initialization process that initializes the various constituent elements (step S (abbreviated to "S" hereinafter) 5). After this, the orientation (tilt) of the brush is detected based on the output of the accelerometer 15 (S10). Next, the CPU 120 estimates the brushing area based at least on the orientation detected in S10 (S20). The CPU 120 then measures the brushing time (S30), estimates the brush angle (S40), and detects the brush pressure (S50). These pieces of information are recorded in the memory 121 on an area-by-area basis (see FIG. 10) and are outputted (S55). The processes from S10 to S55 are repeatedly executed every set period of time. When the power is turned off or the continuous operating time has reached a predetermined amount of time (for example, two minutes), the CPU 120 evaluates the brushing result on an area-by-area basis based on the brushing information (the brushing time, brush angle, and brush pressure) recorded in the memory 121, and outputs the evaluation results to the display device 110 (S60). Note that the brushing information in the memory 121 is cleared every time the electric toothbrush 1 is turned on.

In the present embodiment, the brushing results are outputted at the point in time when the brushing has ended, and the brushing results are also outputted partway through the brushing while the brushing is being carried out.

The various processes shown in FIG. 4 will be described in detail hereinafter.

Orientation Detection

Figure 5:
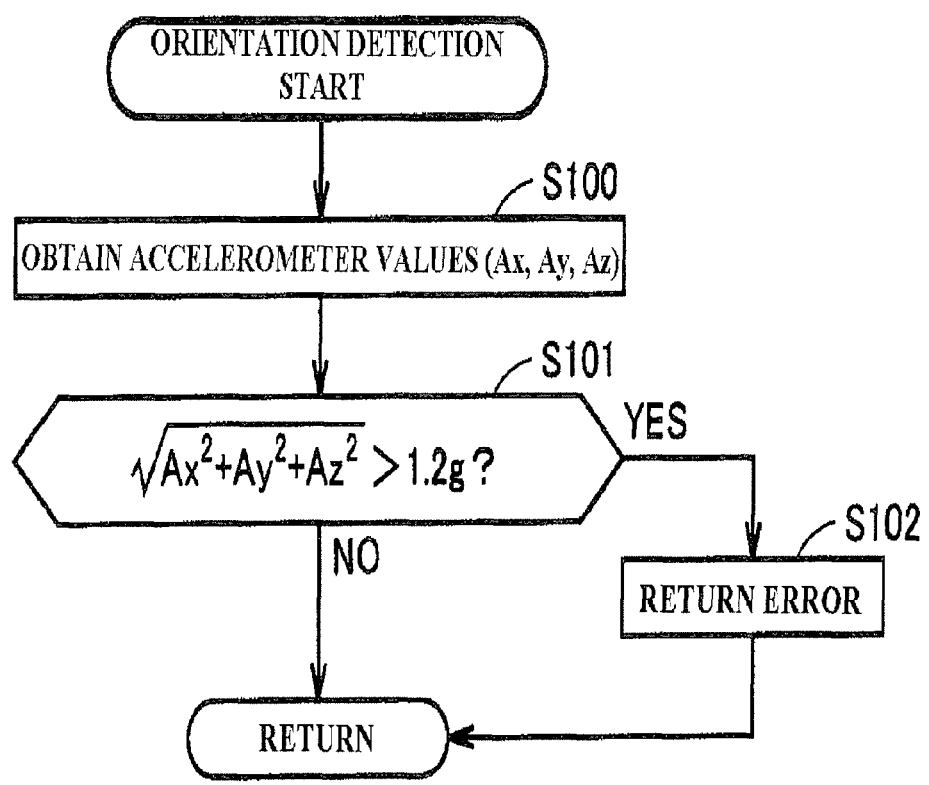
FIG. 5 is a flowchart illustrating an orientation detection process according to the embodiment.

FIG. 5 is a flowchart illustrating the orientation detection process (S10).

The CPU 120 obtains outputs Ax, Ay, and Az for the x, y, and z axes, respectively, from the accelerometer 15 (S100). Ax represents an acceleration component in the x direction, Ay represents an acceleration component in the y direction, and Az represents an acceleration component in the z direction. When the electric toothbrush 1 is at rest (that is, when no dynamic acceleration is acting on the accelerometer 15), a combined vector A of Ax, Ay, and Az corresponds to the gravity acceleration. Here, A=(Ax, Ay, Az) is referred to as an orientation vector.

Here, in the case where the magnitude of the orientation vector A=(Ax, Ay, Az) is greater than 1.2 g (where g represents the gravity acceleration) (S101; YES), an error is returned (S102). This is because it is difficult to accurately identify the direction of the gravity acceleration (that is, the three-dimensional orientation of the brush) when a high dynamic acceleration component is present in the accelerometer output. Note that rather than returning an error as in S102, the processes of S100 and S101 may instead be repeated until accelerometer outputs Ax, Ay, and Az from which a combined vector having a magnitude of less than or equal to 1.2 g is obtained. Note also that the threshold value for determining an error is not limited to 1.2 g, and may be a different value instead.

Estimation of Brushing Area

Figure 6:
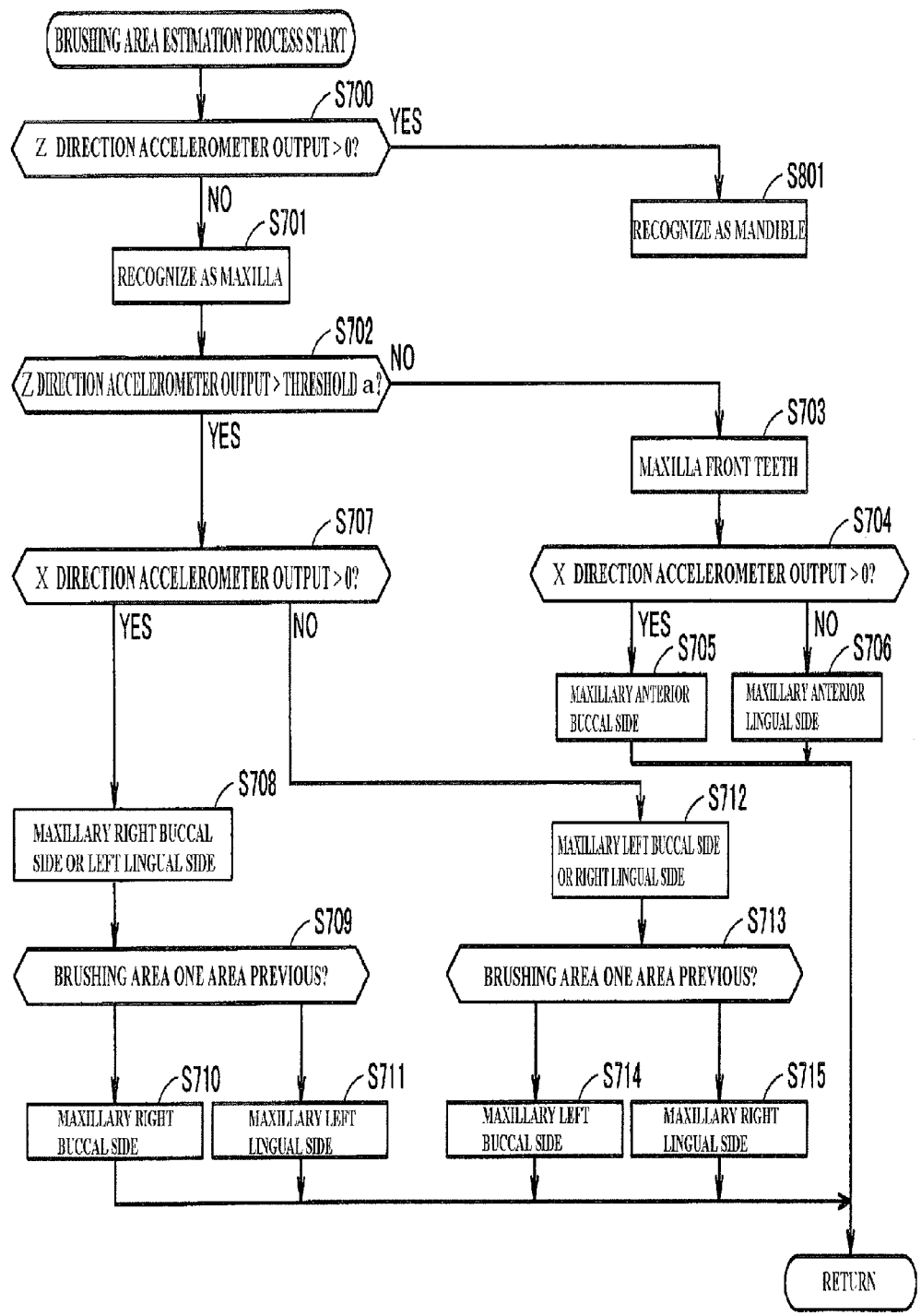
FIG. 6 is a flowchart illustrating a brushing area estimation process (maxilla) according to the embodiment.
Figure 7:
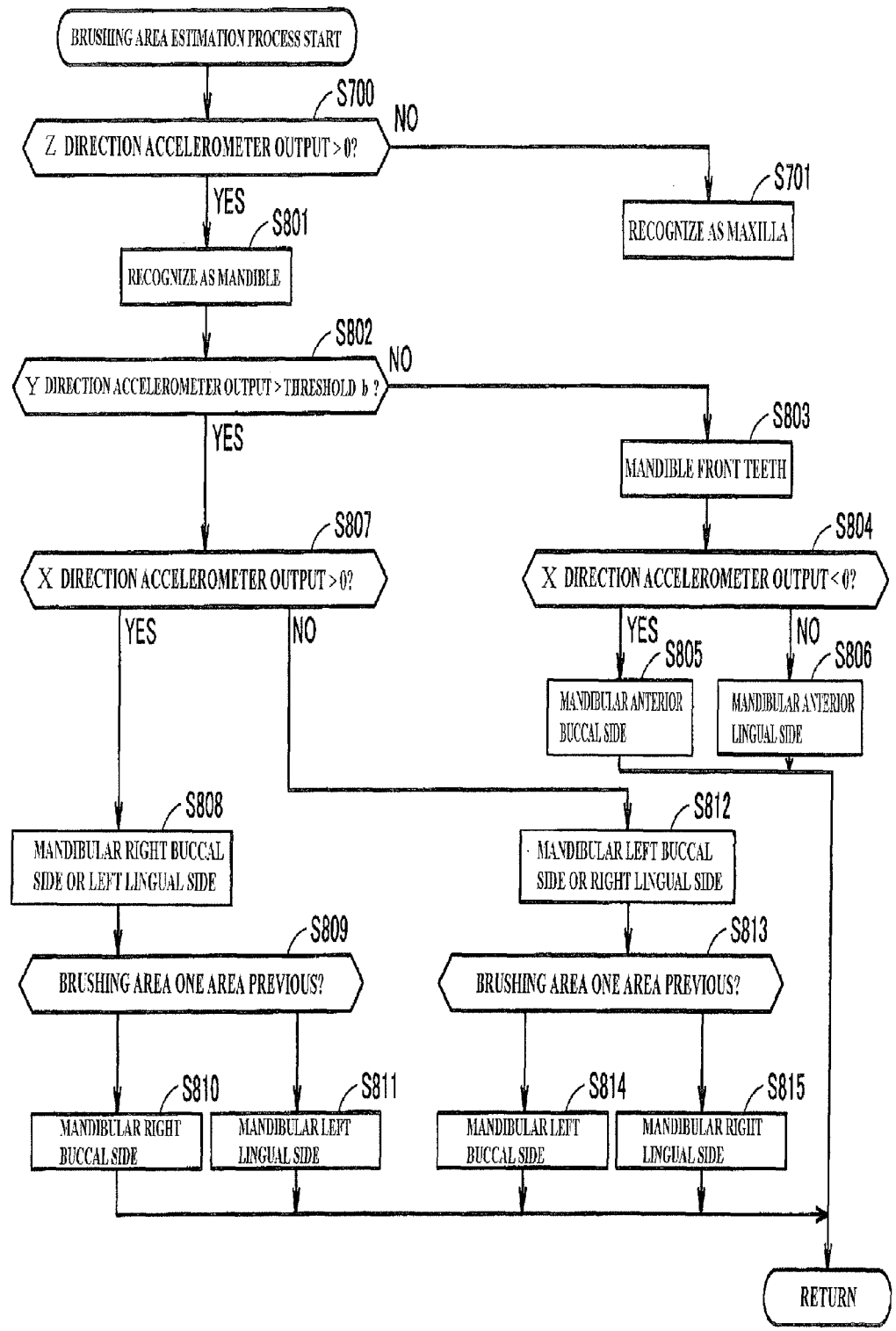
FIG. 7 is a flowchart illustrating a brushing area estimation process (mandible) according to the embodiment.
Figure 8:
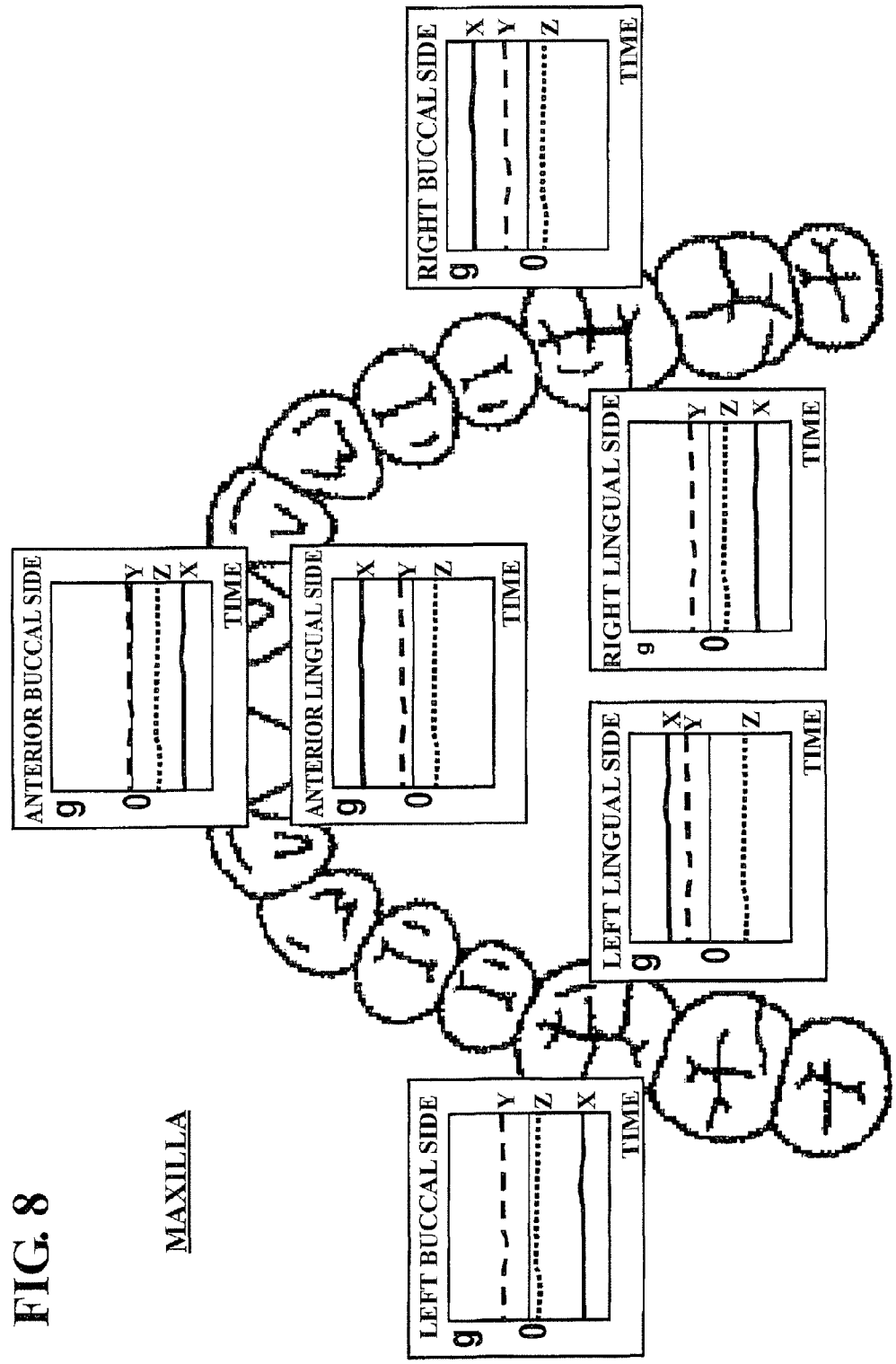
FIG. 8 is a diagram illustrating examples of accelerometer outputs Ax, Ay, and Az for each brushing area in a maxilla.
Figure 9:
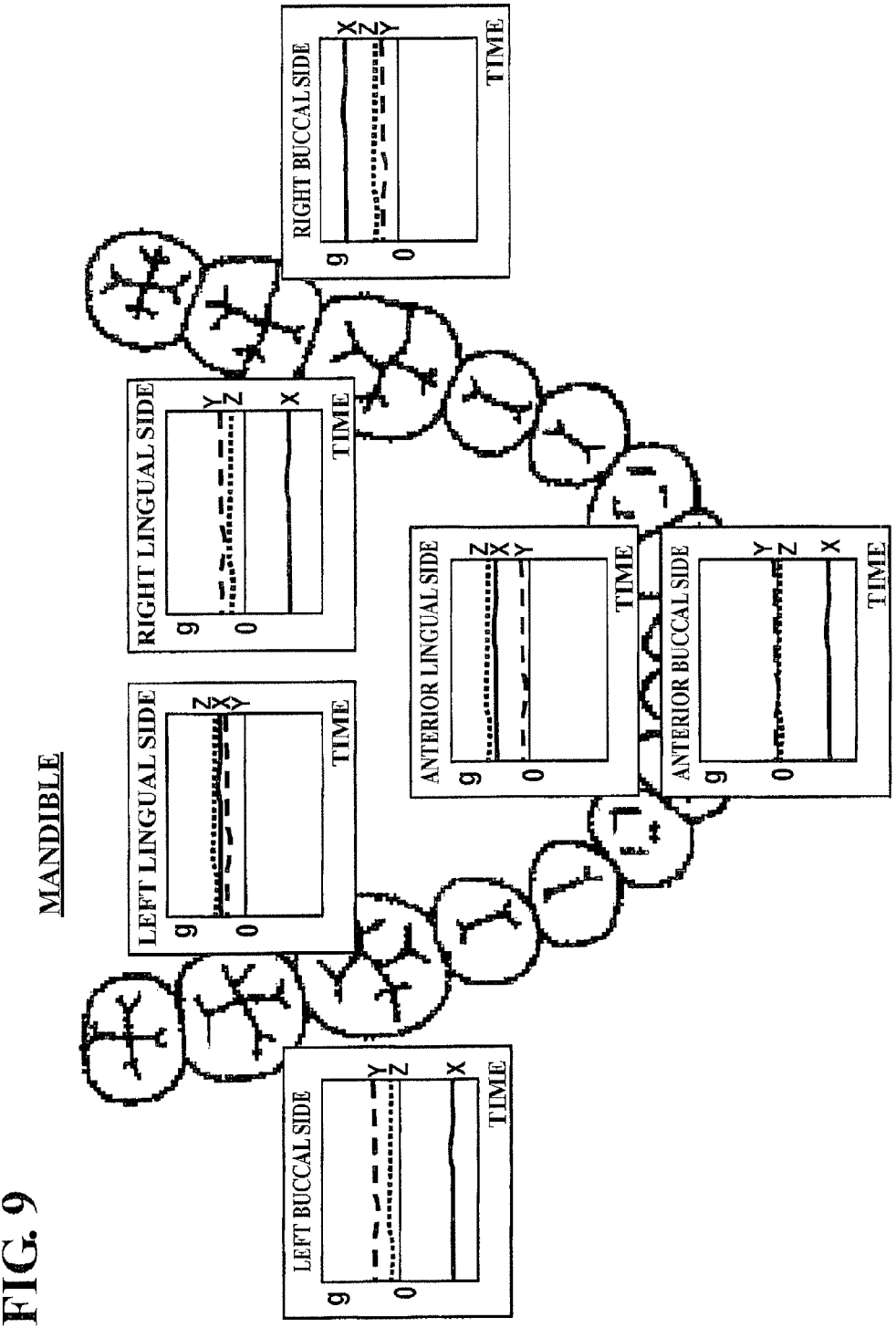
FIG. 9 is a diagram illustrating examples of accelerometer outputs Ax, Ay, and Az for each brushing area in a mandible.

FIGS. 6 and 7 are flowcharts illustrating the brushing area estimation process (S20). Meanwhile, FIGS. 8 and 9 are diagrams illustrating examples of accelerometer outputs Ax, Ay, and Az for the respective brushing areas.

First, the CPU 120 determines whether the brushing area is located at the maxilla or the mandible based on the z direction output Az of the accelerometer (S700). This determination focuses on the fact that when the dentition in the maxilla is being brushed, the brush surface is at least pointed upward, whereas when the dentition in the mandible is being brushed, the brush surface is at least pointed downward. In the case where Az>0, the brushing area is determined to be in the mandible (S801), whereas in the case where Az≤0, the brushing area is determined to be in the maxilla (S701).

(1) Maxilla

The CPU 120 determines whether or not the brushing area corresponds to the front teeth based on the y direction output Ay of the accelerometer (S702). This determination focuses on the fact that although the toothbrush main body 2 is in a comparatively horizontal state when brushing the front teeth, interference with the lips makes it necessary to tilt the toothbrush main body 2 when brushing the molars. The brushing area is determined to correspond to the front teeth of the maxilla in the case where Ay≤a threshold a (S703).

In the case where the brushing area has been determined to correspond to the front teeth of the maxilla, the CPU 120 determines whether the brushing area is on the buccal side or on the lingual side based on the x direction output Ax of the accelerometer (S704). This determination focuses on the fact that the brush faces opposite directions on the buccal side and on the lingual side. The brushing area is determined to correspond to the maxillary anterior buccal side in the case where Ax>0 (S705), whereas the brushing area is determined to correspond to the maxillary anterior lingual side in the case where Ax≤0 (S706).

Meanwhile, in the case where the brushing area has been determined not to correspond to the front teeth of the maxilla in S702, the CPU 120 determines the direction of the brush based on the x direction output Ax of the accelerometer (S707). In the case where Ax>0, the brushing area is determined to correspond to the maxillary right buccal side or the maxillary left lingual side (S708), whereas in the case where Ax≤0, the brushing area is determined to correspond to the maxillary left buccal side or the maxillary right lingual side (S712).

It is difficult to distinguish between the maxillary right buccal side and the maxillary left lingual side, and between the maxillary left buccal side and the maxillary right lingual side, based only on the output of the accelerometer 15. Accordingly, the CPU 120 narrows the brushing area down based on the brushing area determined in the previous process (the process one clock previous) (S709 and S713). Specifically, in S709, if the previous brushing area is the maxillary anterior buccal side, the maxillary right buccal side, the maxillary right lingual side, the mandibular anterior buccal side, the mandibular right buccal side, or the mandibular right lingual side, the current brushing area is estimated to be the maxillary right buccal side (S710), whereas if the previous brushing area is the maxillary anterior lingual side, the maxillary left buccal side, the maxillary left lingual side, the mandibular anterior lingual side, the mandibular left buccal side, or the mandibular left lingual side, the current brushing area is estimated to be the maxillary left lingual side (S711). Likewise, in S713, in the case where the previous brushing area is the maxillary anterior buccal side, the maxillary left buccal side, the maxillary left lingual side, the mandibular anterior buccal side, the mandibular left buccal side, or the mandibular left lingual side, the current brushing area is estimated to be the maxillary left buccal side (S714), whereas if the previous brushing area is the maxillary anterior lingual side, the maxillary right buccal side, the maxillary right lingual side, the mandibular anterior lingual side, the mandibular right buccal side, or the mandibular right lingual side, the current brushing area is estimated to be the maxillary right lingual side (S715). Such estimations hold true because it is highly probable that the brushing area is moved in a manner that reduces to the greatest extent possible the amount of movement of the brush, changes in the direction of the brush, and so on.

(2) Mandible

The CPU 120 determines whether or not the brushing area corresponds to the front teeth based on the y direction output Ay of the accelerometer 15 (S802). This determination focuses on the fact that although the toothbrush main body 2 is in a comparatively horizontal state when brushing the front teeth, interference with the lips makes it necessary to tilt the toothbrush main body 2 when brushing the molars. The brushing area is determined to correspond to the front teeth of the mandible in the case where Ay≤a threshold b (S803).

In the case where the brushing area has been determined to correspond to the front teeth of the mandible, the CPU 120 determines whether the brushing area is on the buccal side or on the lingual side based on the x direction output Ax of the accelerometer (S804). This determination focuses on the fact that the brush faces opposite directions on the buccal side and on the lingual side. In the case where Ax<0, the brushing area is determined to correspond to the mandibular anterior buccal side (S805), whereas in the case where Ax≥0, the brushing area is determined to correspond to the mandibular anterior lingual side (S806).

Meanwhile, in the case where the brushing area has been determined not to correspond to the front teeth of the mandible in S802, the CPU 120 determines the direction of the brush based on the x direction output Ax of the accelerometer (S807). In the case where Ax>0, the brushing area is determined to correspond to the mandibular right buccal side or the mandibular left lingual side (S808), whereas in the case where Ax≤0, the brushing area is determined to correspond to the mandibular left buccal side or the mandibular right lingual side (S812).

In S809, if the previous brushing area is the mandibular anterior buccal side, the mandibular right buccal side, the mandibular right lingual side, the mandibular anterior buccal side, the maxillary right buccal side, or the maxillary right lingual side, the current brushing area is estimated to be the mandibular right buccal side (S810), whereas if the previous brushing area is the mandibular anterior lingual side, the mandibular left buccal side, the mandibular left lingual side, the maxillary anterior lingual side, the maxillary left buccal side, or the maxillary left lingual side, the current brushing area is estimated to be the mandibular left lingual side (S811). Likewise, in S813, in the case where the previous brushing area is the mandibular anterior buccal side, the mandibular left buccal side, the mandibular left lingual side, the maxillary anterior buccal side, the maxillary left buccal side, or the maxillary left lingual side, the current brushing area is estimated to be the mandibular left buccal side (S814), whereas if the previous brushing area is the mandibular anterior lingual side, the mandibular right buccal side, the mandibular right lingual side, the maxillary anterior lingual side, the maxillary right buccal side, or the maxillary right lingual side, the current brushing area is estimated to be the mandibular right lingual side (S815).

Through the aforementioned processes, the current brushing area is specified as the maxillary anterior buccal side (S705), the maxillary anterior lingual side (S706), the maxillary right buccal side (S710), the maxillary left lingual side (S711), the maxillary left buccal side (S714), the maxillary right lingual side (S715), the mandibular anterior buccal side (S805), the mandibular anterior lingual side (S806), the mandibular right buccal side (S810), the mandibular left lingual side (S811), the mandibular left buccal side (S814), or the mandibular right lingual side (S815).

Note that the stated determination algorithm is merely an example, and any determination algorithm may be employed as long as it is capable of detecting a brushing area from the outputs Ax, Ay, and Az of the accelerometer 15. For example, rather than using the values of Ax, Ay, and Az directly as the variables for the determination, two-dimensional variables obtained by combining Ax, Ay, and Az as appropriate may be used in the determination instead. The two-dimensional variables can be set as desired, such as Ay/Az, Ax·Ax+Ay·Ay, Az−Ax, and so on. Alternatively, the brushing area may be determined after converting the acceleration information Ax, Ay, and Az from the respective axes into angle information (orientation angles) α, β, and γ. The angle of the x axis relative to the gravity acceleration direction may be defined as a roll angle α, the angle of the y axis relative to the gravity acceleration direction may be defined as a pitch angle β, and the angle of the z axis relative to the gravity acceleration direction may be defined as a yaw angle γ. The thresholds used in the determinations can be set based on the results of clinical experiments or the like.

Brushing Time Measurement

FIG. 10 illustrates an example of brushing information recorded in the memory 121. FIG. 10 shows an example of a state in which the mandibular left buccal side is being brushed. Here, it is assumed that the maxillary anterior buccal side has been brushed for 7.5 seconds prior to the mandibular left buccal side, and that the maxillary left buccal side is being brushed for 12.2 seconds. Note that a "-" indicates that no data is recorded, or in other words, that the area in question has not yet been brushed.

In S30 of FIG. 4, the CPU 120 counts up the brushing time for the brushing area estimated in S20 (the mandibular left buccal side, in the example shown in FIG. 10). For example, if the processes from S10 to S50 in FIG. 4 are executed once every 0.1 seconds, the brushing time for the mandibular left buccal side is counted up by 0.1, and is thus 2.1 seconds.

Note that the cumulative brushing time is recorded as the brushing information. In other words, in the case where, for example, the brushing area has moved to the maxillary left buccal side for a second time, the brushing time stored in the memory is not reset; instead, the brushing time is added to the value stored in the memory, i.e., a brushing time of 12.2 seconds.

Brush Angle Estimation

In S40 of FIG. 4, the CPU 120 estimates the brush angle based on the orientation detected in S10 (that is, the output of the accelerometer 15), and updates the value of the brush angle for the current brushing area (the mandibular left buccal side, in the example shown in FIG. 9). At this time, it is preferable for the CPU 120 to calculate and record an average value for the brush angle from the value of the brush angle stored in the memory and the value estimated as described here.

Figure 11A:
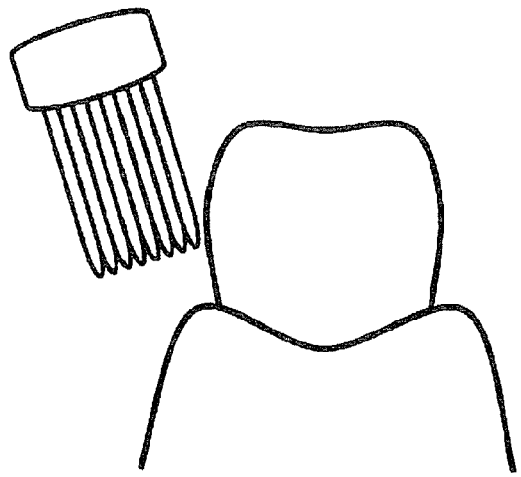
FIGS. 11A, 11B, and 11C are diagrams illustrating brush angles.
Figure 11B:
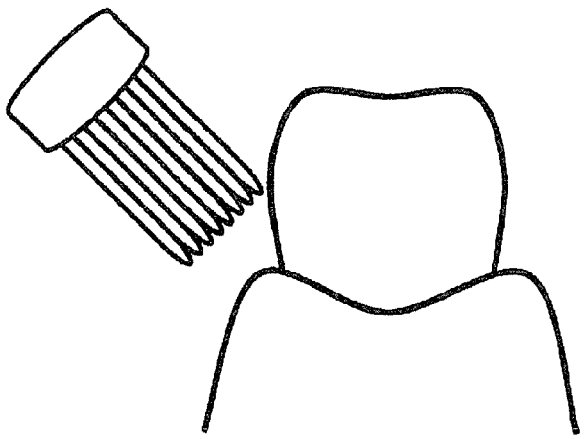
Figure 11C:
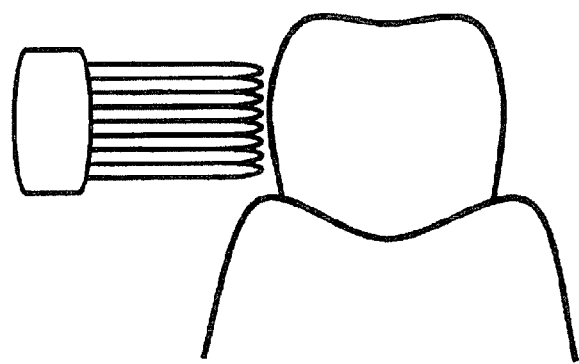

The brush angle is the angle at which the brush makes contact with the tooth axis (that is, the axis that spans from the crown to the root of the tooth). FIG. 11A illustrates a state in which the brush angle is 15°, FIG. 11B illustrates a state in which the brush angle is 45°, and FIG. 11C illustrates a state in which the brush angle is 90°. In order to effectively remove food residue, plaque, and so on from the periodontal pockets, from between the teeth, and so on, it is preferable to move the brush so that the tips of the bristles enter into the periodontal pockets, between the teeth, and so on. Therefore, it is preferable for the brush angle to be within a range from 35° to 55°.

Figure 12:
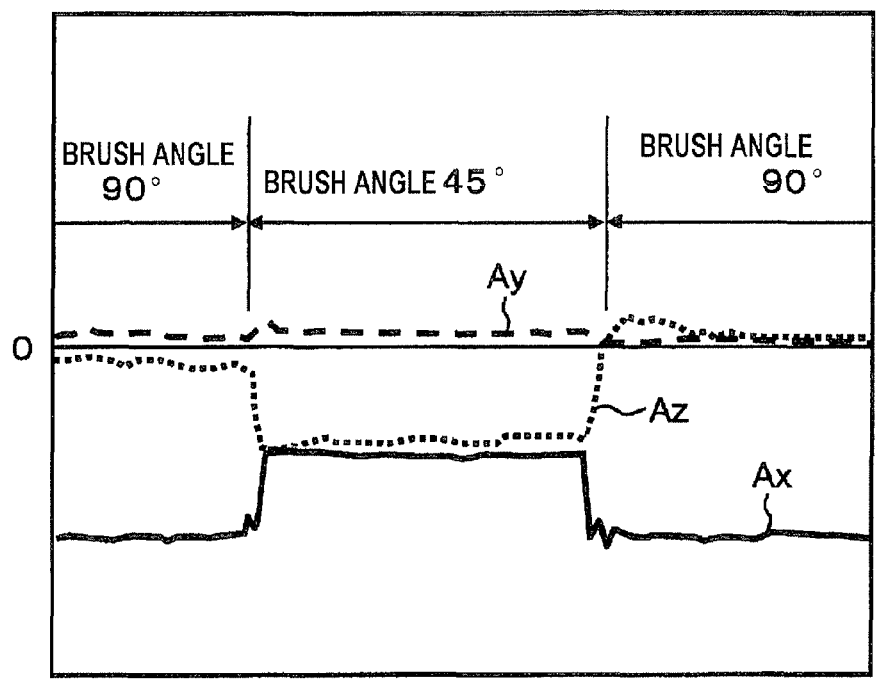
FIG. 12 is a diagram illustrating waveform changes in sensor outputs resulting from changes in the brush angle.

The brush angle can be estimated, for example, from the z direction acceleration component Az. This is because as shown in FIG. 12, the value of Az changes significantly in accordance with the brush angle, with Az being almost 0 in the case where the brush angle is approximately 90° and increasing as the brush angle decreases. Note that the x direction acceleration component Ax also changes in accordance with the brush angle, and thus it is also favorable to estimate the brush angle based on Ax instead of Az, estimate the brush angle based on both Ax and Az (that is, based on the direction of the combined vector of Ax and Az), and so on. The length for which the brush angle continues may also be calculated, or the brush angle may be estimated in a general manner, such as "less than 35°", "between 35° and 55°", "greater than or equal to 55°", and so on.

Brush Pressure Detection

In S50 of FIG. 4, the CPU 120 estimates (detects) the brush pressure based on the output of the accelerometer 15, and updates the value of the brush pressure for the current brushing area (the mandibular left buccal side, in the example shown in FIG. 10). At this time, it is preferable for the CPU 120 to calculate and record an average value for the brush pressure from the value of the brush pressure stored in the memory 121 and the value detected as described here.

Too low a brush pressure reduces the effectiveness of plaque removal, and conversely, too high a brush pressure may result in problems such as a reduction in the lifespan of the brush, an increase in the burden on the gums, and so on. Because the electric toothbrush 1 requires a lower brush pressure than normal toothbrushes, it is said that almost all people who have begun using an electric toothbrush 1 tend to apply too much brush pressure. The optimal value for the brush pressure is approximately 100 g to 200 g.

Details of the estimation of the brush pressure according to the present embodiment will be described later.

Evaluation/Output of Brushing Results

Based on the brushing information recorded in the memory 121 in S55 or S60 of FIG. 4, the CPU 120 evaluates the brushing results on an area-by-area basis, and outputs the evaluation results to the display device 110 (the display 111).

Figure 13:
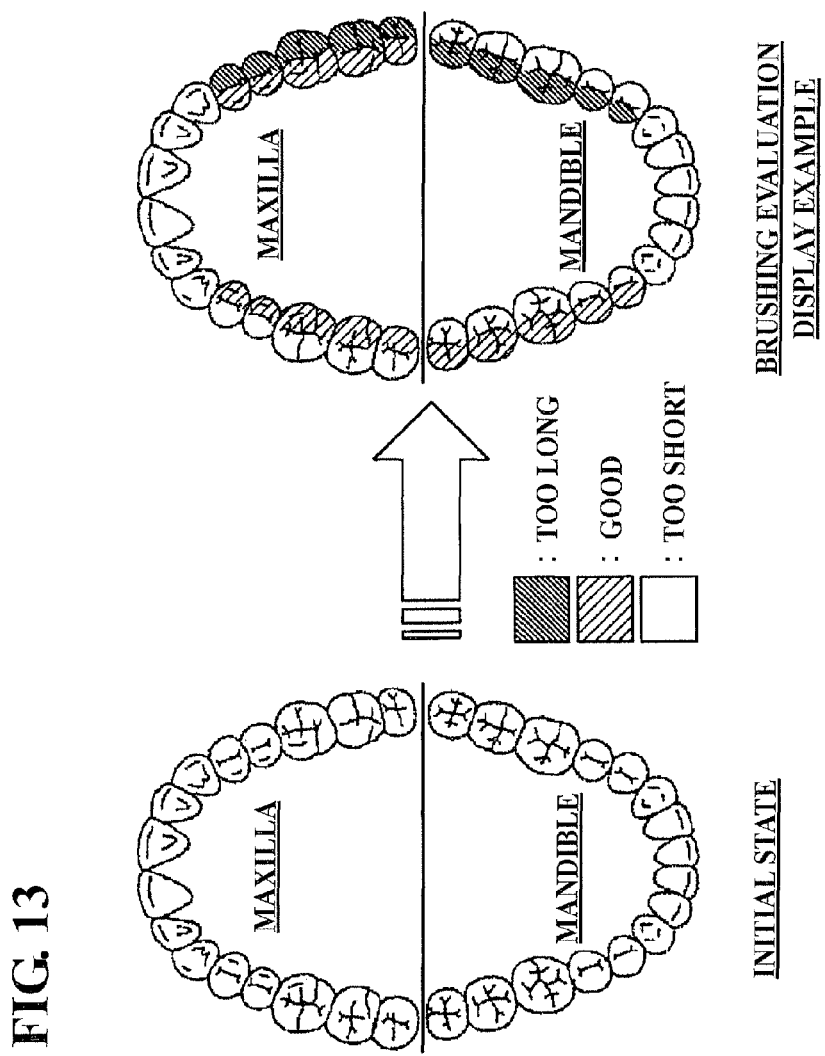
FIG. 13 is a diagram illustrating an example of the output of a brushing time serving as a brushing result.

FIG. 13 is an example of the output of an evaluation result for the brushing time. The CPU 120 loads the brushing time for each area from the memory 121, and evaluates, for example, less than 7 seconds as "too short", 7 to 15 seconds as "good", and more than 15 seconds as "too long". These evaluation results are then sent to the display device 110. The dentition is displayed in the display 111 of the display device 110, and the areas within the dentition are indicated by colors that correspond to evaluation results ("too short" by white, "good" by yellow, "too long" by red, and so on). By checking this display, the user can intuitively grasp which area of the dentition has not been brushed enough (or has been brushed too much).

FIG. 14 is an example of the output of an evaluation result for the brush angle. For example, the brush angle is evaluated in three stages, or "less than 35°", "35° to 55°", and "greater than 55°", and the various areas in the dentition are indicated by colors that correspond to the evaluation results. Because the effectiveness of plaque removal is lower when brushing is carried out at an improper brush angle than when brushing is carried out at a proper brush angle, there is the possibility that the desired brushing results will not be obtained, the brushing will take more time, and so on. As shown in FIG. 14, if brush angle evaluations are outputted for each area, the user can be made aware of how to brush using the proper brush angle.

Figure 15:
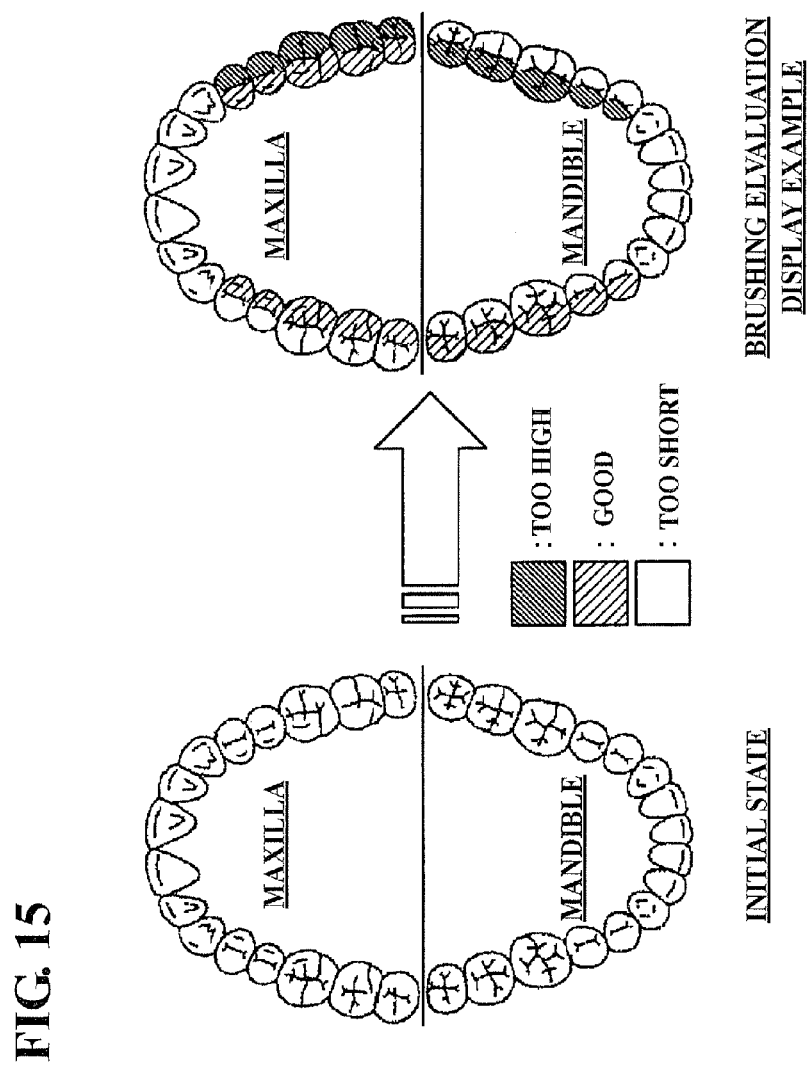
FIG. 15 is a diagram illustrating an example of the output of a brush pressure serving as a brushing result.

FIG. 15 is an example of the output of an evaluation result for the brush pressure. For example, the brush pressure is evaluated as "too low" for less than 100 g, "good" for 100 g to 200 g, and "too high" for more than 200 g, and the various areas in the dentition are indicated by colors that correspond to the evaluation results. If the brush pressure is improper as described above, there is the possibility that problems such as a drop in the effectiveness of plaque removal, a decrease in the lifespan of the brush, an increase in the burden on the gums, and so on will occur. However, it is difficult for the user to understand how much pressure corresponds to the optimum brush pressure. With respect to this point, if brush pressure evaluations are outputted for each area as shown in FIG. 15, the user can be informed of the proper brush pressure, and can thus be made aware of how to brush with the proper brush pressure.

Figure 16:
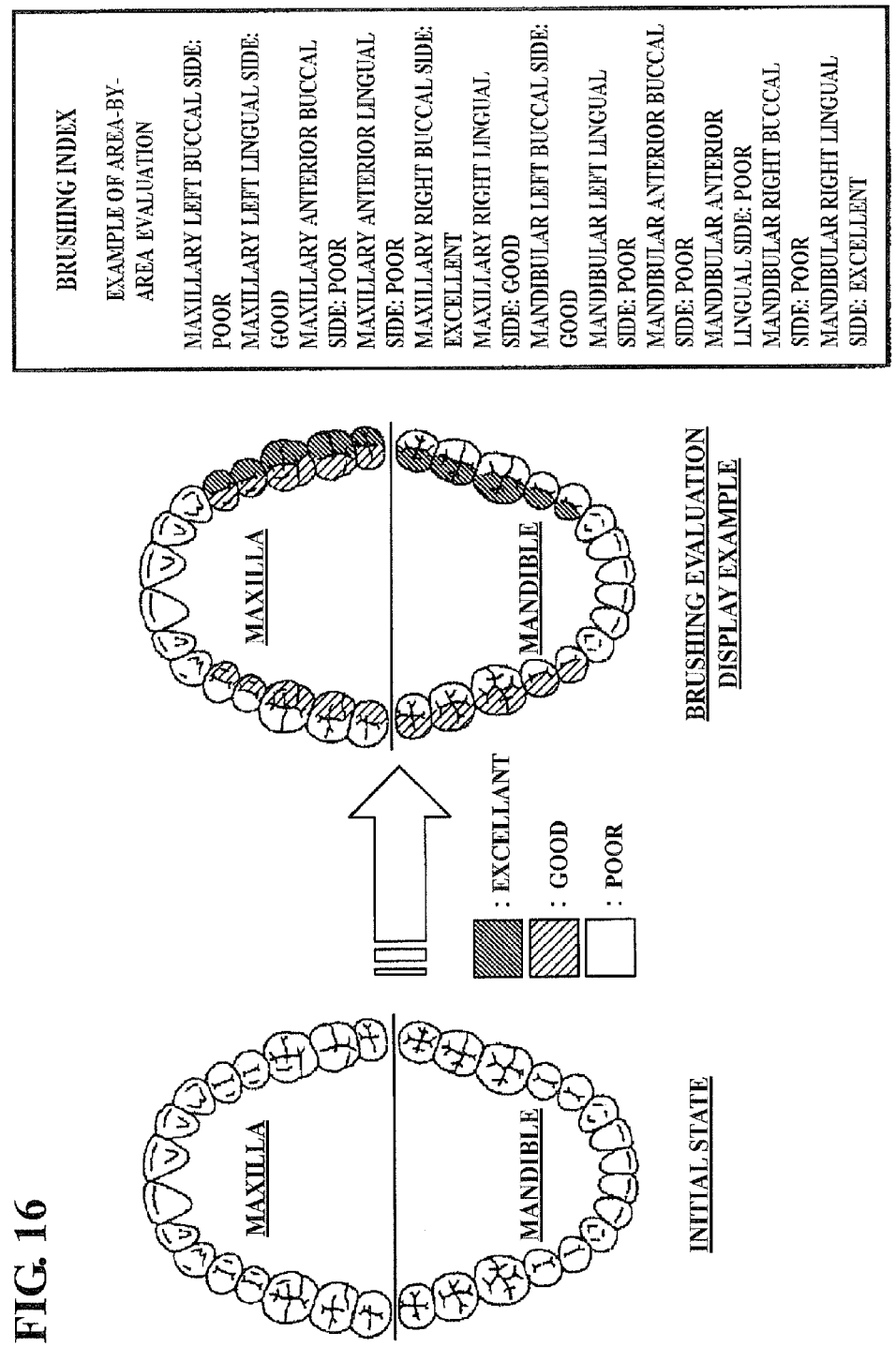
FIG. 16 is a diagram illustrating an example of the output of a brushing index serving as a brushing result.

FIG. 16 is an example of the output of an evaluation result for a brushing index. The brushing index is an index for collectively evaluating multiple evaluation items (brushing time, brush angle, and brush pressure), and indicates an achievement level for brushing. The formulas for calculating the brushing index may be defined in any manner. In the present embodiment, the brushing time and brush pressure are evaluated with a maximum of 35 points each and the brush angle is evaluated with a maximum of 30 points, and the total of those evaluation values (a maximum of 100 points) is used as the brushing index. The brushing index (points) is then evaluated based on three levels, or "excellent", "good", and "poor". Here, for the brushing index, more than 80 points is called "excellent", 60 to 80 points is called "good", and less than 60 points is called "poor".

The left side of FIG. 16 indicates an initial state found prior to brushing, whereas the right side indicates the post-brushing evaluation in association with the respective areas of the dentition in the jaws that are displayed schematically. Outputting this type of overall evaluation provides the user with more valuable guidelines regarding his or her brushing.

As described thus far, the orientation of the electric toothbrush 1 and the brushing area can be identified with a high level of precision by using the output of the accelerometer 15. Therefore, brushing results can be evaluated for detailed segments (areas), and useful and reliable evaluation guidelines can be provided to the user. Furthermore, the present embodiment is advantageous in that the accelerometer 15 is small and can thus easily be incorporated into the main body of the electric toothbrush 1.

Note that the evaluation results from FIGS. 13 to 16 may be displayed simultaneously in the display 111, or may be displayed in sequence. In the case of the latter, the display may be switched automatically, or may be switched through the user manipulating a button.

Furthermore, in the above embodiment, the results are automatically displayed when the electric toothbrush 1 is turned off. However, because it can be assumed that brushing may be carried out in a different location than where the display device 110 is installed, it is preferable, for example, to provide a function so that the brushing information is sent to the display device 110 from the toothbrush main body 2 when the user presses a button provided in the display device 110 or the toothbrush main body 2 and the results are then displayed in the display device 110.

It is preferable for the brushing information, evaluation results, and so on accumulated in the memory 121 to be printable. For example, a printer (not shown) may be provided in the charger, the display device, or the like, or the configuration may be such that print data can be transmitted to an external printer from the toothbrush main body, the charger, the display device, and so on. Furthermore, it is preferable to provide a function for transferring data such as the brushing information, evaluation results, or the like to an external device (a personal computer, a mobile telephone, a PDA (personal digital assistant), or the like) (not shown) through wireless communication or hard-wired communication. In addition, a memory card slot (not shown) may be provided in the toothbrush main body, the charger, the display device, or the like, and data such as the brushing information, evaluation results, or the like may then be capable of being recorded in an external memory card.

In addition, the configuration may be such that optimum values (target values) for the brushing time, brush angle, and brush pressure can be set to different values on an area-by-area basis. For example, although a brush angle of 35° to 55° is preferable in order for the tips of the bristles to effectively remove food residue, plaque, or the like from the periodontal pockets, from between the teeth, and so on when brushing the tooth surfaces (side surfaces) of the molars, a greater angle (for example, 55° to 90°) is preferable when brushing the front teeth, which have comparatively larger tooth surfaces. Meanwhile, a brush angle of approximately 0° is preferable for the occlusal surfaces of the molars. Furthermore, the optimum brushing time, brush angle, and brush pressure can also be determined in view of avoiding damaging structures such as the gums, rather than in view of the effectiveness of cleaning. More useful and reliable evaluation guidelines can be provided if evaluation is carried out having determined the optimum values on an area-by-area basis in such a manner.

Brush Pressure Estimation

With the electric toothbrush 1, the brush pressure is estimated by focusing on the fact that the vibration frequency fluctuates in accordance with the load placed on the motor 10, or in other words, in accordance with the brush pressure, even if a constant driving signal is supplied to the motor 10. The vibration frequency decreases as the brush pressure increases, and the vibration frequency increases as the brush pressure decreases.

In S50 of FIG. 4, the brush pressure is detected (estimated) using Ax, Ay, or Az, which are the voltage signals outputted from the accelerometer 15.

Figure 17:
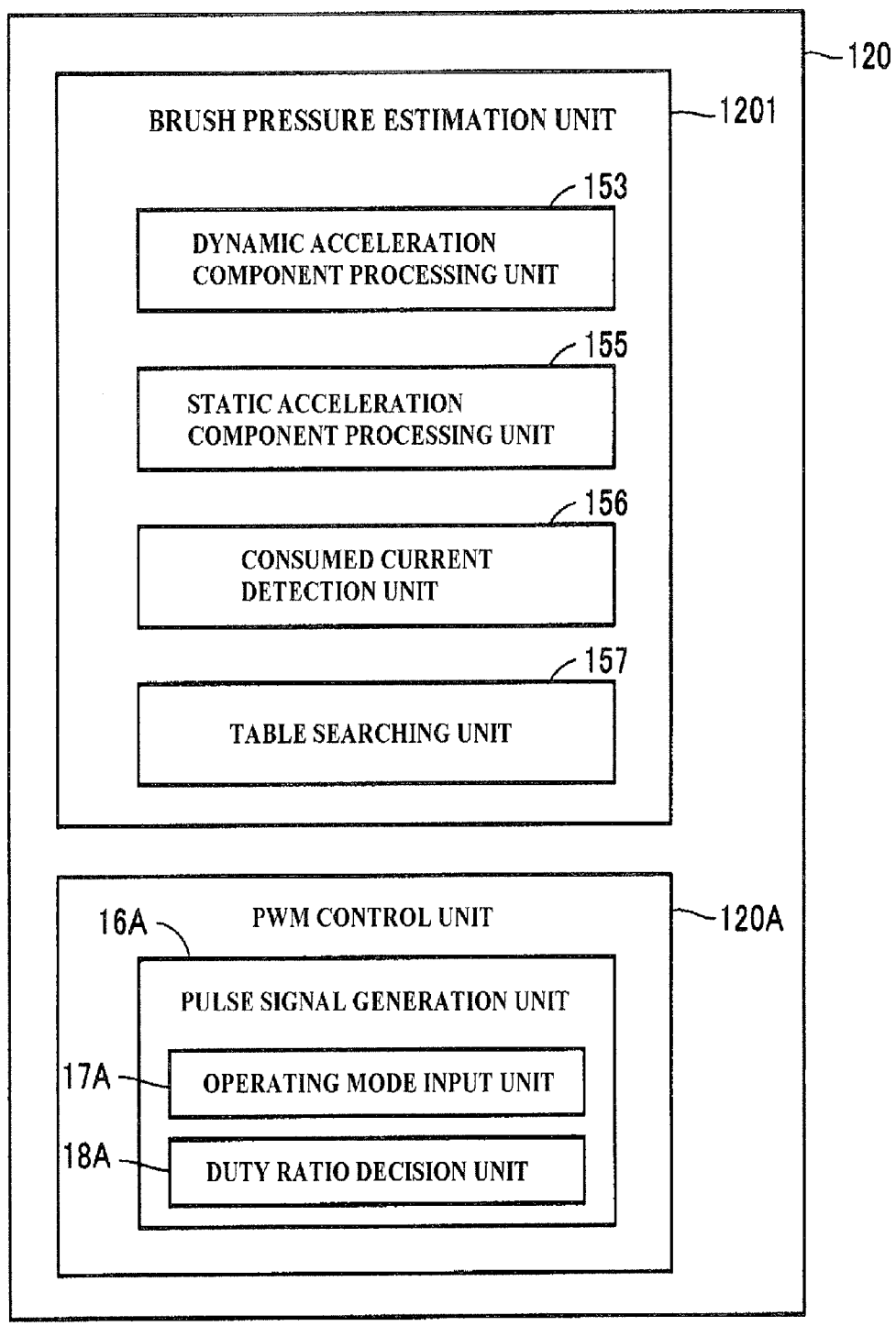
FIG. 17 is a diagram illustrating a functional configuration for estimating a brush pressure according to the embodiment.

FIG. 17 illustrates a functional configuration for estimating the brush pressure according to the embodiment. The respective units shown in FIG. 17 are realized by combining programs whose executions are controlled by the CPU 120 with circuits. These programs are stored in advance in a predetermined region of the memory 121. The functions of the various units are realized by the CPU 120 reading out the programs from the memory 121 and executing the command codes of the programs that have been read out.

As shown in FIG. 17, the CPU 120 includes a brush pressure estimation unit 1201 for estimating the brush pressure and a PWM control unit 120A for driving the motor 10 in accordance with PWM control.

The brush pressure estimation unit 1201 includes: a dynamic acceleration component processing unit 153 and a static acceleration component processing unit 155 that process signals of the dynamic acceleration component and a static acceleration component of the electric toothbrush 1 from the signals outputted by the accelerometer 15; a consumed current detection unit 156 that is inputted with the signal outputted from the current detection unit 104 that indicates the current consumed by (current supplied to) the motor 10 and detects the current consumed by the motor 10 based on the inputted signal; and a table searching unit 157 that searches a table TB1 in the memory 121 and outputs the result of the search.

The PWM control unit 120A includes a pulse signal generation unit 16A that generates a pulse signal for controlling the driving of the motor 10. The pulse signal generation unit 16A generates a pulse signal using a pulse signal generation circuit (not shown). The pulse signal generation unit 16A has an operating mode input unit 17A that inputs an operating mode specified by the user manipulating the switch S, and a duty ratio decision unit 18A that determines a duty ratio for the pulse signal based on the inputted operating mode. The pulse signal generation unit 16A generates and outputs a pulse signal having the determined duty ratio. The outputted pulse signal is supplied to the motor 10 as a driving signal.

Figure 18:
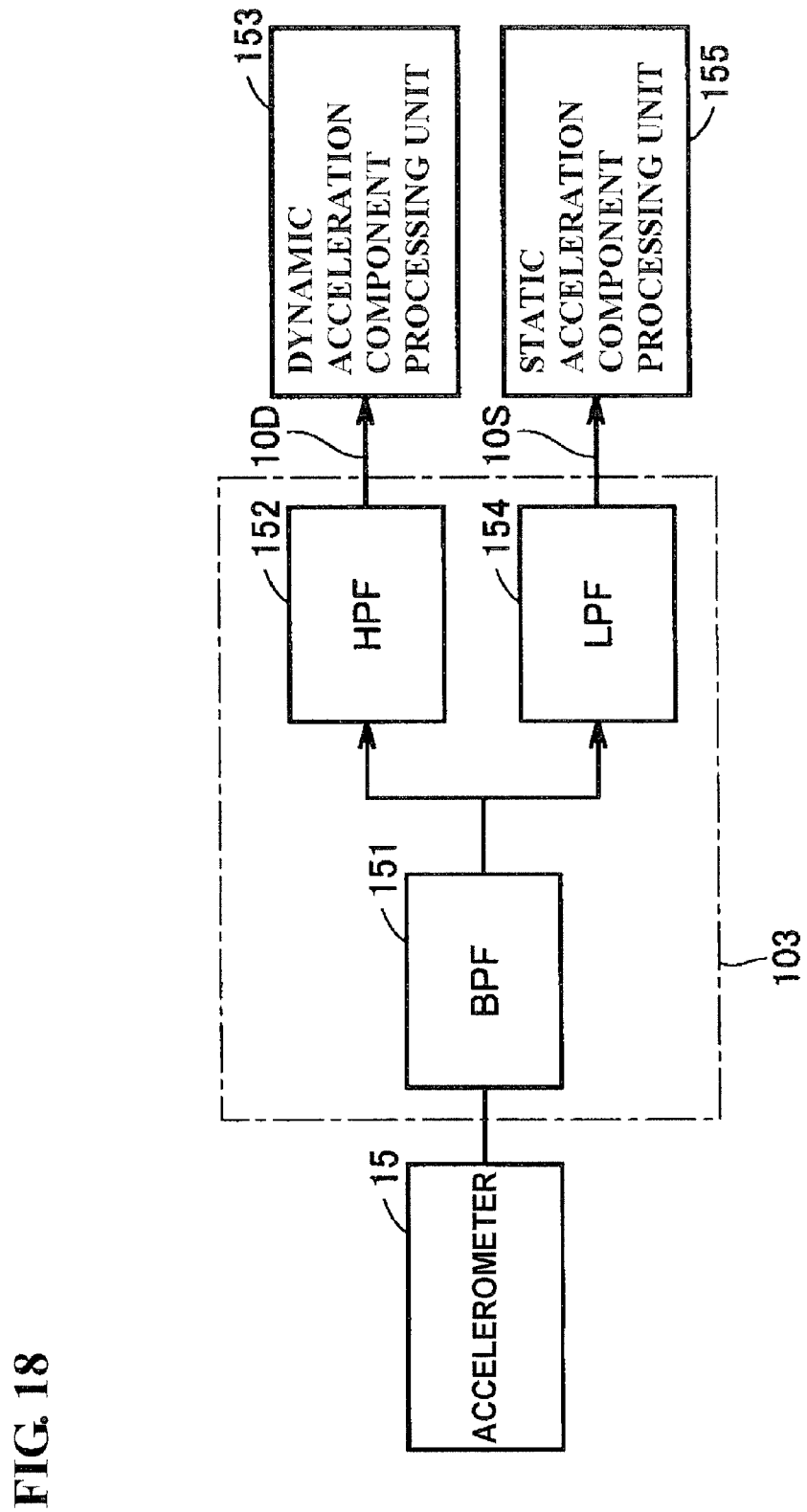
FIG. 18 is a schematic diagram illustrating an accelerometer and its surrounding circuitry.

FIG. 18 schematically illustrates the accelerometer 15 and the surrounding circuitry thereof. As shown in FIG. 18, the filter unit 103 is connected to the output stage of the accelerometer 15. The filter unit 103 includes: a BPF (Band Pass Filter) 151 that takes the signal outputted by the accelerometer 15 as its input and allows only a predetermined frequency band of the signal to pass; and a HPF (High Pass Filter) 152 and LPF (Low Pass Filter) 154 connected in parallel to the output stage of the BPF 151. The dynamic acceleration component processing unit 153 is connected to the output stage of the HPF 152, whereas the static acceleration component processing unit 155 is connected to the output stage of the LPF 154.

Of the signal inputted from the BPF 151, the HPF 152 allows only frequencies of the signal that are greater than or equal to a predetermined cutoff frequency (for example, 90 Hz) to pass, and outputs those frequencies. Of the signal inputted from the BPF 151, the LPF 154 allows only frequencies of the signal that are less than a predetermined cutoff frequency (for example, several Hz) to pass, and outputs those frequencies.

The dynamic acceleration component processing unit 153 detects the vibration frequency of the main body of the electric toothbrush 1 caused by the rotational operation of the motor 10 by taking a signal 10D outputted from the HPF 152 as an input and processing that signal. The signal 10D outputted from the HPF 152 corresponds to a signal of the vibration frequency (for example, the 100 Hz to 300 Hz frequency band) resulting from the rotation (vibration) of the motor 10. The static acceleration component processing unit 155 takes a signal 10S outputted from the LPF 154 as an input and processes that signal. This input signal 10S corresponds to a signal of the vibration frequency (for example, a frequency band of several Hz) resulting from the user altering the orientation of the brush, such as twisting the electric toothbrush 1, during brushing. Accordingly, the signal 10S corresponds to a signal indicating an orientation information component of the main body of the electric toothbrush 1.

Vibration Frequency Detection (A) in FIG. 19 indicates an example, over time, of the waveform of the signal outputted by the BPF 151 shown in FIG. 18. In (A) of FIG. 19, the signal 10D (indicated by a thin solid line in FIG. 19) of the vibration component caused by the rotational operation of the motor 10, which is a high-frequency component from 100 Hz to 300 Hz, overlaps with the signal 10S (indicated by a bold solid line in FIG. 19), which is a low-frequency component of less than several Hz; however, passing the signals through the stated filter unit 103 makes it possible to output the signals 10D and 10S separately. In (B) of FIG. 19, the signal 10D from a given time period in (A) of FIG. 19 is indicated in an enlarged state.

A procedure for detecting the vibration frequency will be described with reference to (B) of FIG. 19. The dynamic acceleration component processing unit 153 takes the signal 10D as an input and detects the slope of the waveform of the inputted signal 10D for each predetermined cycle T (called a "sampling cycle T" hereinafter). This slope can be detected by carrying out a differential process on the waveform. The dynamic acceleration component processing unit 153 detects the slope (a positive slope or a negative slope) of the waveform of the signal 10D in each sampling cycle T, and detects the length of a period for which the positive slope continues or the length of a period for which the negative slope continues, as well as the timing at which the positive slope changes to the negative slope (or the negative slope changes to the positive slope). The frequency of the signal 10D, or in other words, the vibration frequency of the electric toothbrush 1, is detected based on the result of this detection. The detected vibration frequency is outputted to the table searching unit 157.

The method for detecting the vibration frequency is not limited to the method indicated in (B) of FIG. 19. For example, limit values (maximal values and minimal values) may be detected by carrying out a differential process on the waveform of the signal 10D, and the frequency of the signal 10D, or in other words, the vibration frequency, may be detected based on the number of maximal values and minimal values detected within a predetermined time period.

Detection of Brush Pressure Based on Vibration Frequency

The graph in FIG. 20 illustrates a correlation relationship between the vibration frequency and a load (here, the brush pressure). The graph in FIG. 20 indicates data based on the results of experiments carried out by the inventors. In this graph, the vertical axis represents the vibration frequency (Hz), whereas the horizontal axis represents the magnitude of a load placed on the motor 10 (grams; g).

The motor 10 rotates at the highest velocity when unloaded (that is, when there is no load), but the rotational velocity decreases as the load increases, when a constant driving signal is supplied from the PWM control unit 120A.

Specifically, in an unloaded state, the vibration frequency of the electric toothbrush 1 caused by the rotation of the motor 10 is at a maximum vibration frequency V1, but when a load is placed on all of the bristles 210, such as when pushing the bristles 210 against the teeth, the brush pressure increases. As a result, the load on the motor 10 increases, the rotational velocity of the motor 10 decreases, and the vibration frequency drops. For example, in the case where the brush pressure is 100 to 200 g (an appropriate pressure), the vibration frequency of the motor 10 is detected in the range of appropriate pressure vibration frequencies V2 to V3. Furthermore, if the bristles 210 are pushed firmly against the teeth and an excessive load of, for example, 500 g is exerted on all of the bristles 210, the maximum load is placed on the motor 10, and the vibration frequency transitions to a range of excessive pressure vibration frequencies V4 to 0.

If the correlation relationship shown in FIG. 20 is followed, the brush pressure can be uniquely determined (detected) based on the frequency of the signal 10D, or in other words, based on the vibration frequency.

In the present embodiment, data of the vibration frequency indicated by the properties of the graph in FIG. 20 and data of the corresponding brush pressure are stored in advance in the table TB1, in association with each other. The table searching unit 157 searches the table TB1 based on the vibration frequency outputted by the dynamic acceleration component processing unit 153, and reads out the brush pressure corresponding to that vibration frequency from the table TB1 based on the search result. Through this, the brush pressure estimation unit 1201 can detect (estimate) the brush pressure.

Overall Process for Brush Pressure Estimation

Figure 21:
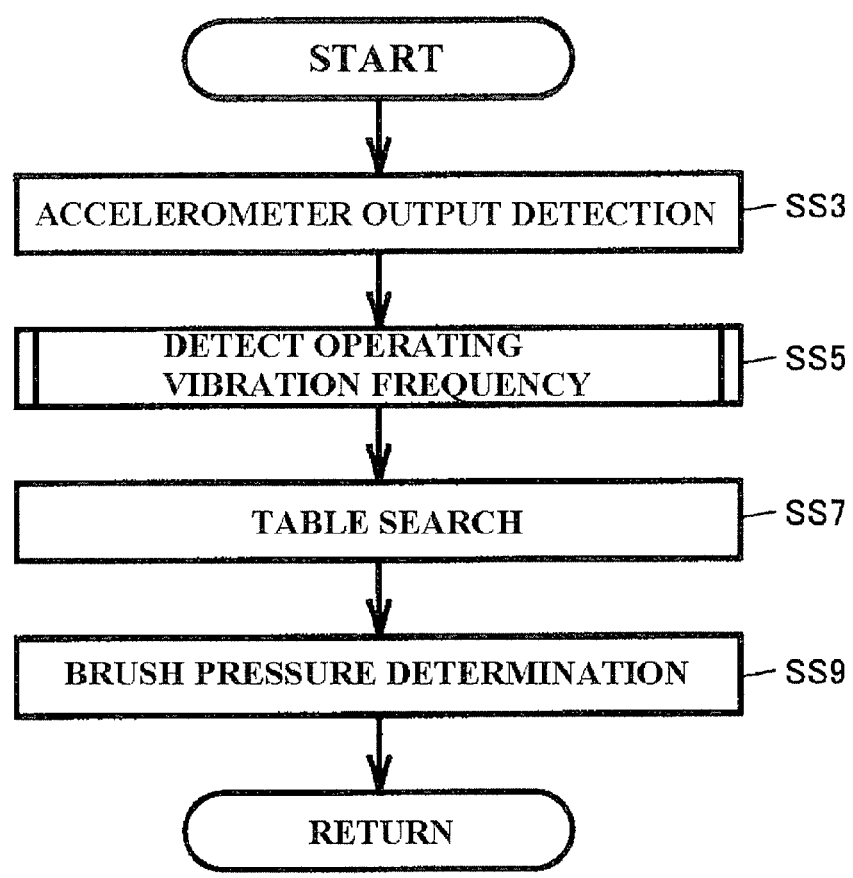
FIG. 21 is a general flowchart illustrating a brush pressure detection (estimation) process according to the embodiment.

FIG. 21 is a general flowchart illustrating a brush pressure detection (estimation) process according to the present embodiment.

As shown in FIG. 21, the brush pressure estimation unit 1201 is inputted with the signal outputted by the accelerometer 15 via the filter unit 103 (step SS (abbreviated to "SS" hereinafter) 3). The dynamic acceleration component processing unit 153 detects the vibration frequency in accordance with the procedure described above (the vibration frequency detection) (SS5). Next, the table searching unit 157 searches the table (SS7) based on the vibration frequency detected in step SS5 in accordance with the procedure described above (the detection of the brush pressure based on the vibration frequency), and detects the brush pressure (SS9). The brush pressure is determined (estimated) as a result.

Other Methods for Brush Pressure Estimation

Although the brush pressure estimation unit 1201 estimates the brush pressure based only on the vibration frequency of the motor 10 in the aforementioned procedure, the vibration frequency may be detected based on the current supplied to the motor 10.

Figure 22:
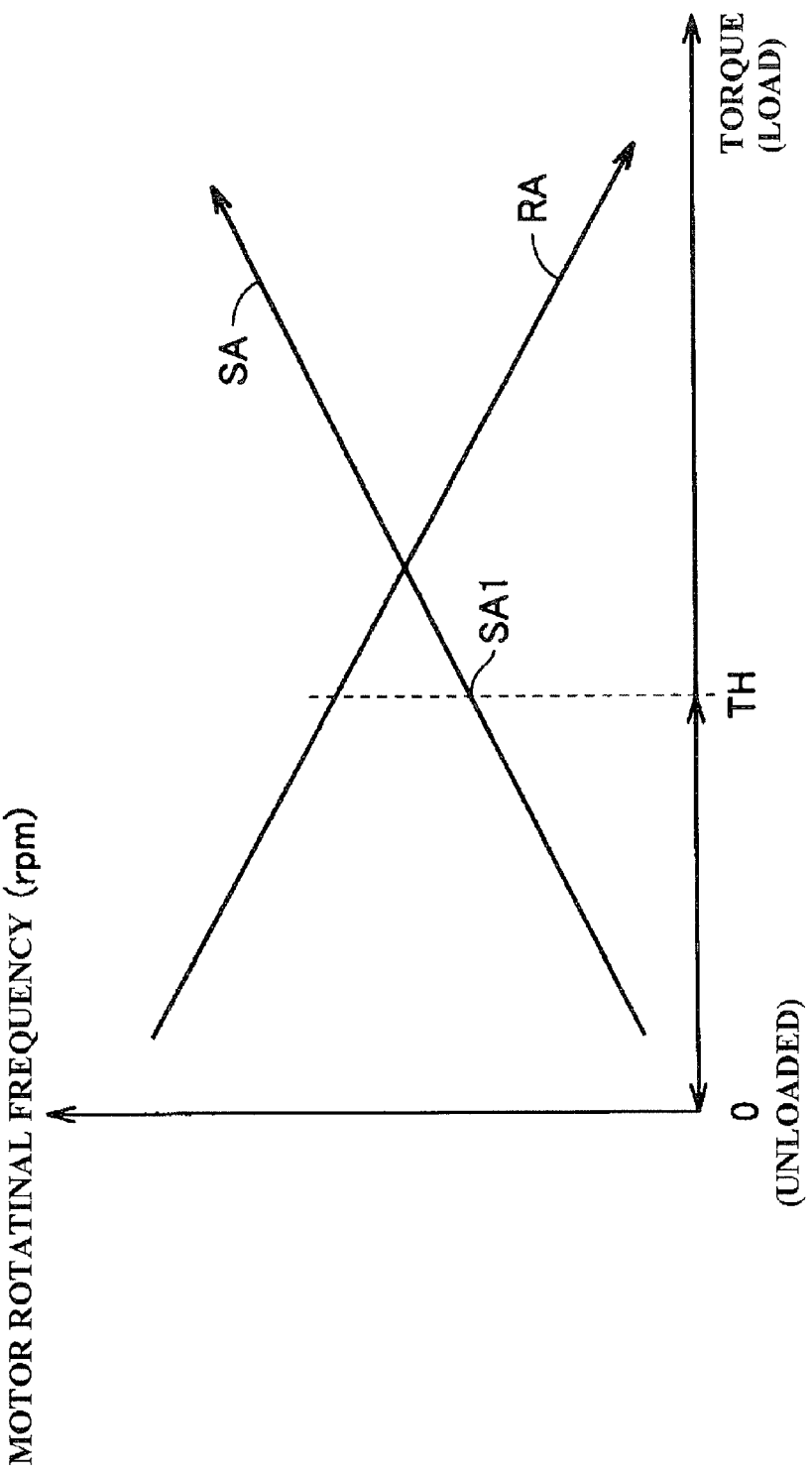
FIG. 22 is a diagram illustrating load properties of a motor according to the embodiment.

FIG. 22 is a graph illustrating load properties of the motor 10 according to the present embodiment. In the graph shown in FIG. 22, the vertical axis represents the rotational frequency (rpm) of the motor 10 and the current supplied to the motor 10 (in other words, the current consumed by the motor 10 (unit: A). The horizontal axis represents the torque (load) exerted on the motor 10. This torque corresponds to the stated brush pressure. A straight line SA in FIG. 22 expresses an ideal property in which the current supplied to the motor 10 increases as the torque (load) increases. A straight line RA, meanwhile, expresses a property in which the rotational frequency of the motor 10 decreases as the torque (load) increases. Here, data of the supplied current indicated by the straight line SA and data of the corresponding torque are detected in advance through experimentation, and are stored in association with each other in a table TB2.

The current supplied to the motor 10 is detected by the consumed current detection unit 156 using the current detection unit 104. The current detection unit 104 corresponds to a resistance element connected to the input stage of the driving signal of the motor 10. The consumed current detection unit 156 detects the current supplied to the motor 10 by measuring the voltage at the resistance element and dividing the measured voltage by the resistance value of the resistance element. Note that the detection may be carried out using a current sensor rather than using the resistance value.

With the DC motor employed as the motor 10, the current supplied to the motor 10 increases as the torque increases from 0, as indicated by the straight line SA; here, the motor 10 produces heat as the current supplied thereto increases. In other words, assuming that a current of a value SA1 is supplied to the motor 10 when the torque is at a predetermined value TH (>0), when the torque exceeds the predetermined value TH, an increasing amount of the current supplied to the motor 10 (>SA1) is consumed by the production of heat, and the straight line SA no longer expresses the ideal correlation relationship shown in FIG. 22.

Therefore, during periods in which the torque is comparatively low, such as periods where a current corresponding to a torque of 0 to TH is supplied, it is possible to detect the brush pressure based on the current supplied to the motor 10 by following the relationship between the current supplied to the motor 10 indicated by the straight line SA and the torque. During periods where the torque is greater than the predetermined value TH, or in other words, during periods where a current greater than the current value SA1 is being supplied, the brush pressure is detected by searching the table TB1 based on the vibration frequency as mentioned above, rather than based on the consumed current. Note that the current value SA1 is detected in advance through experimentation, and is stored in the memory 121.

During operations, the brush pressure estimation unit 1201 compares the current value detected by the consumed current detection unit 156 and the current value SA1 read out from the memory 121, and controls the table searching unit 157 based on the result of the comparison.

In other words, based on the result of the comparison, during periods in which it is determined that, a current less than or equal to the current value SA1 is being supplied, the table searching unit 157 is controlled to search the table TB2 based on the value of the current consumed by the motor 10 as detected by the consumed current detection unit 156. Based on the result of the detection, the table searching unit 157 reads out the corresponding torque (brush pressure) from the table TB2. On the other hand, based on the result of the comparison, during periods in which it is determined that a current greater than the current value SA1 is being supplied, the table searching unit 157 is controlled to search the table TB1 based on the vibration frequency, as described earlier. Based on the result of the detection, the table searching unit 157 reads out the corresponding brush pressure from the table TB1. Through this, the brush pressure estimation unit 1201 can accurately estimate the brush pressure based on the current supplied to the motor 10, the vibration frequency, or both.

Compensation for Power Supplied to Motor 10

Based on an understanding that it is necessary to improve the vibration frequency detection accuracy in order to more accurately estimate the brush pressure, the inventors discovered that an increase in the load (an increase in the brush pressure) and the lifespan of the battery are causes for a drop in the rotational frequency of the motor 10, or in other words, the vibration frequency.

Accordingly, in the present embodiment, the power supplied to the motor 10 from the rechargeable battery 13 is compensated for in order to maintain a constant level of power. This makes it possible to eliminate a factor in the drop in the vibration frequency caused by the battery lifespan.

Figure 23:
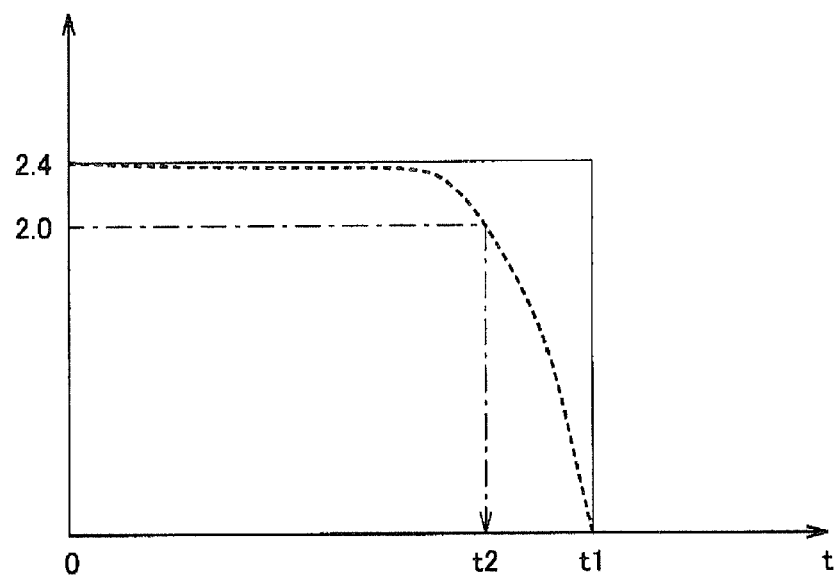
FIG. 23 is a diagram schematically illustrating a change over time in the voltage outputted by a rechargeable battery.

FIG. 23 schematically illustrates a change over time in the output voltage of the rechargeable battery 13. Here, the output voltage indicates the remaining charge in the rechargeable battery 13. The graph in FIG. 23 indicates properties obtained through experimentation; the vertical axis expresses the output voltage of the battery (unit: V), whereas the horizontal axis represents elapsed time t.

A nickel hydride battery is typically used as the rechargeable battery 13 for the electric toothbrush 1. It is assumed that the output rating of the rechargeable battery 13 is, for example, 2.4 V. Upon first using the rechargeable battery 13 that has been charged, the output voltage can be maintained at the output rating of 2.4 V; however, as the usage time increases, the output voltage drops. Assuming an ideal battery that has no excess discharge, the output voltage stays at the output rating (2.4 V) until the end of the battery's life (a time t1), and the output voltage drops to 0 when the time t1 has been reached, as indicated by the solid line in FIG. 23. However, batteries generally do not have such ideal properties. In other words, as indicated by the broken line in FIG. 23, the rechargeable battery 13 gradually becomes unable to maintain the output rating of 2.4 V, and the output voltage drops to 2.0 V when the time elapsed since usage began has reached a time t2 (<t1), after which the output voltage drops quickly. When the output voltage of the rechargeable battery 13 drops to 2.0 V or less, the electric toothbrush 1 cannot achieve sufficient operational performance, and thus a sufficient vibration frequency cannot be obtained.

Figure 24:
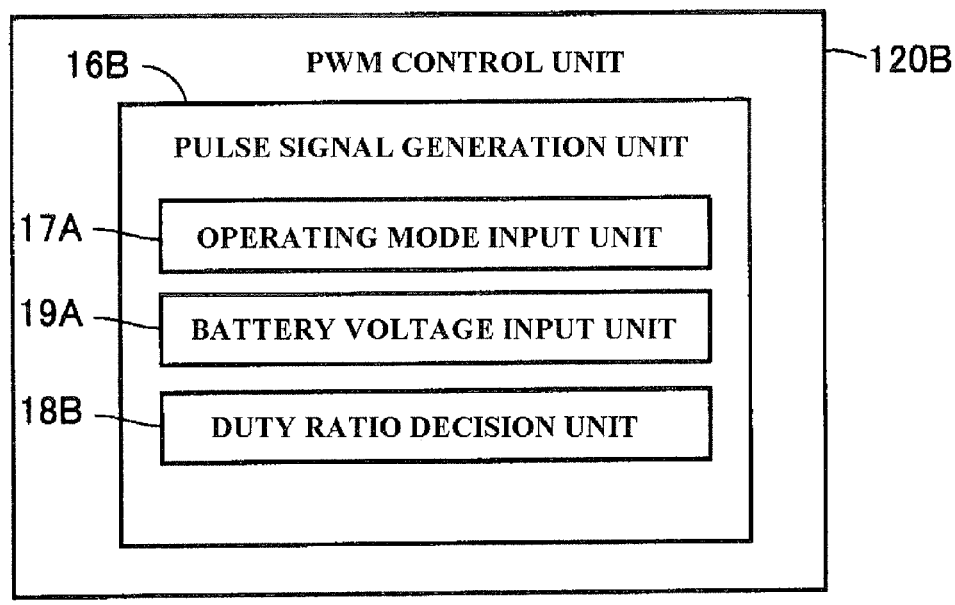
FIG. 24 is a diagram illustrating another configuration of a PWM control unit.

Accordingly, the CPU 120 includes a PWM control unit 120B, as shown in FIG. 24, in place of the PWM control unit 120A shown in FIG. 17. As shown in FIG. 24, the PWM control unit 120B includes a pulse signal generation unit 16B that generates a pulse signal for controlling the driving of the motor 10. The pulse signal generation unit 16B generates a pulse signal using a pulse signal generation circuit (not shown). The pulse signal generation unit 16B, meanwhile, includes: an operating mode input unit 17A that inputs an operating mode specified by the user manipulating the switch S; a battery voltage input unit 19A that is inputted with a detection signal from the voltage monitor 102 and detects the output voltage of the rechargeable battery 13 based on the detection signal; and a duty ratio decision unit 18B that determines a duty ratio for the pulse signal based on the operating mode and the output voltage of the rechargeable battery 13. The pulse signal generation unit 16B generates and outputs a pulse signal having the determined duty ratio. The pulse signal is supplied to the motor 10 as a driving signal.

Figures 25, 26:
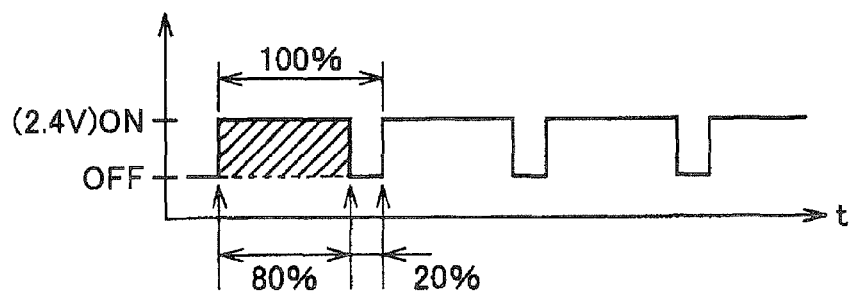
FIG. 25 is a diagram illustrating changes in the duty ratio of a pulse signal.
FIG. 26 is a diagram illustrating an example of a table referred to by a duty ratio decision unit.

Next, changes in the duty ratio of the pulse signal used in the PWM control will be described with reference to FIG. 25. In FIG. 25, the horizontal axis represents time, whereas the vertical axis represents the on/off level (voltage) of the pulse signal. The power supplied to the motor 10 is determined by the product of the length of the on period of the pulse signal and the voltage corresponding to "on" (voltage x time), as indicated by the hatched area in FIG. 25. Accordingly, in the present embodiment, the duty ratio decision unit 18B changes the duty ratio of the pulse signal so that the power supplied to the motor 10 (voltage x time) is constant. Here, the "duty ratio" refers to the length of the period for which the voltage level is at "on" relative to the length of a single cycle of the pulse signal in the case where the length of the single cycle is taken as 100%. By changing the duty ratio, the power supplied to the motor 10 can be kept constant even if the output voltage of the rechargeable battery 13 drops, which in turn makes it possible to maintain the vibration frequency.

FIG. 26 illustrates an example of a table TB3 referred to by the duty ratio decision unit 18B in order to change the duty ratio. Duty ratios DR for keeping the power supplied to the motor 10 are held in the table TB3 in correspondence with respective combinations of operating mode types MD for the electric toothbrush 1 and output voltage values BV for the rechargeable battery 13. The data in the table TB3 is obtained in advance through experimentation. Here, 2.4 V, 2.2 V, and 2 V are held as the output voltage values BV, and three operating modes, or a "high" mode that vibrates at a high velocity, a "medium" mode that vibrates at a lower velocity, and a "low" mode that vibrates at an even lower velocity, are held as the operating mode types MD. Note that the numbers of the types of output voltage values BV and the operating mode types MD that are held are not limited to those described here.

During operation, the operating mode input unit 17A inputs the type of the operating mode specified by the user manipulating the switch S, and the battery voltage input unit 19A detects the output voltage of the rechargeable battery 13. The duty ratio decision unit 18B searches the table TB3 shown in FIG. 26 based on the combination of the inputted operating mode type and the detected output voltage. The duty ratio DR corresponding to the stated combination is read out from the table TB3 based on the result of the detection. The pulse signal generation unit 16B generates and outputs a pulse signal having the duty ratio DR that has been read out. The outputted pulse signal is supplied to the motor 10 as a driving signal.

By changing the duty ratio DR in this manner, a drop in the vibration frequency caused by a decrease in the output voltage (remaining charge) of the rechargeable battery 13 can be eliminated, which in turn makes it possible to detect the brush pressure accurately.

Brush Pressure Detection

An example in which the brush pressure is accurately detected based on the vibration frequency, without compensating for the power supplied to the motor 10 as described earlier, will be described next.

Figure 27:
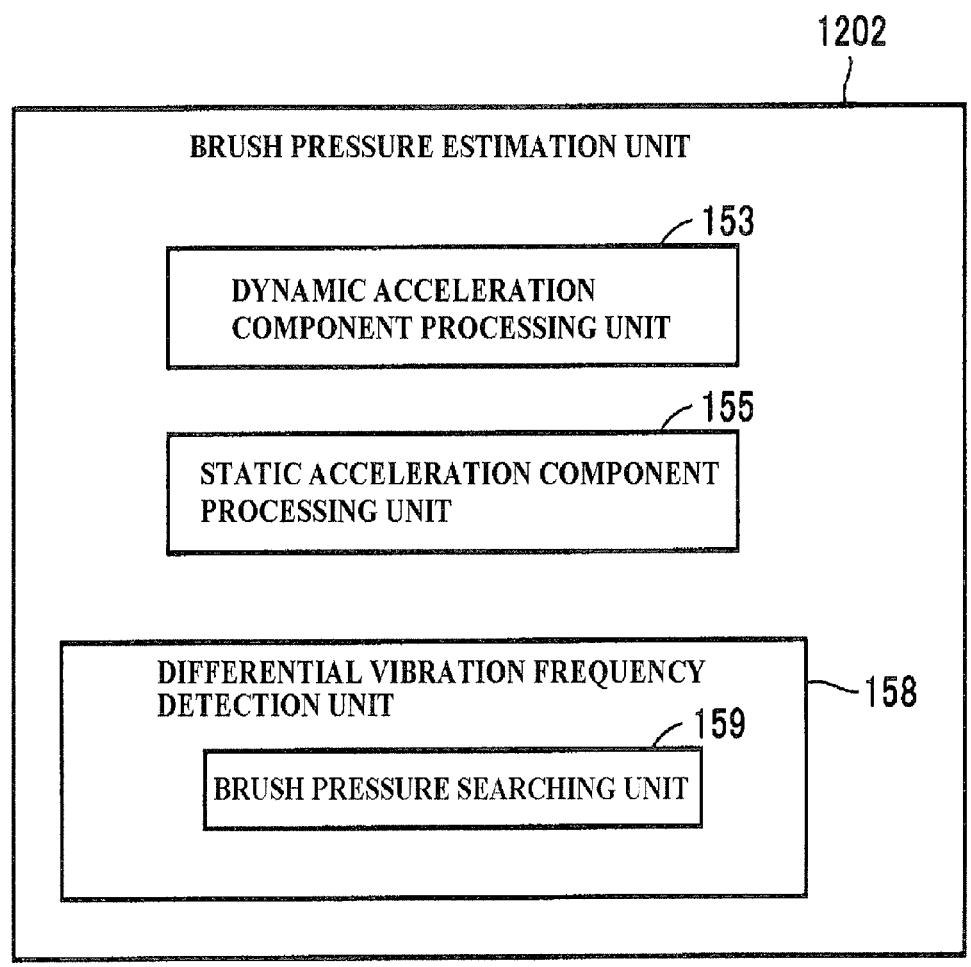
FIG. 27 is a diagram illustrating the functional configuration of a brush pressure estimation unit provided with a function for finding a brush pressure.

FIG. 27 illustrates the functional configuration of a brush pressure estimation unit 1202 that includes a brush pressure search function. The brush pressure estimation unit 1202 may be used in place of the brush pressure estimation unit 1201 shown in FIG. 17. The brush pressure estimation unit 1202 includes the dynamic acceleration component processing unit 153, the static acceleration component processing unit 155, and a differential vibration frequency detection unit 158 that has a brush pressure searching unit 159. Aside from the differential vibration frequency detection unit 158, the configuration of the brush pressure estimation unit 1202 is the same as the brush pressure estimation unit 1201, and thus descriptions thereof will be omitted.

The differential vibration frequency detection unit 158 is inputted with a vibration frequency (Hz) outputted from the dynamic acceleration component processing unit 153, and detects a difference between the inputted vibration frequency and the unloaded vibration frequency. The brush pressure is then detected based on the detected difference. The brush pressure is estimated in this manner.

Figure 29:
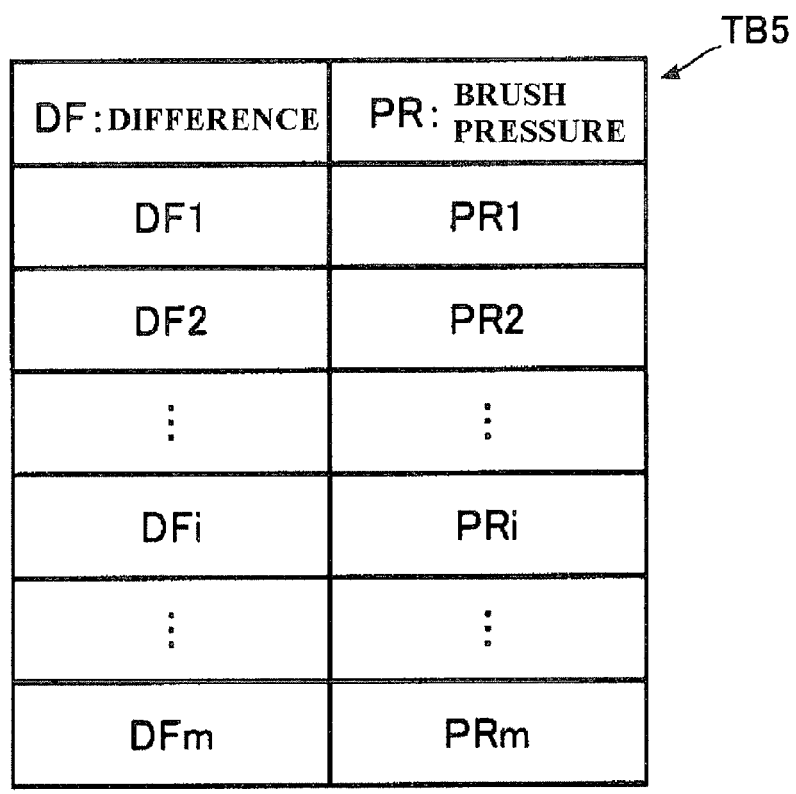
FIG. 29 is a diagram illustrating an example of a table referred to in order to find a brush pressure.

In order to detect the brush pressure, the brush pressure searching unit 159 searches the tables TB4 and TB5 shown in FIGS. 28 and 29. Vibration frequencies (Hz) DV when the load upon the motor 10 is 0 (unloaded) are held in advance in the table TB4 shown in FIG. 28 in correspondence with respective combinations of the operating mode types MD for the electric toothbrush 1 and the output voltage values BV for the rechargeable battery 13. The numbers of the operating mode types MD and the types of output voltage values BV that are held in the table TB4 are not limited to those described here.

The table TB5 shown in FIG. 29 holds, in advance, differences DF between the vibration frequencies DV read out from the table TB4 and the vibration frequencies detected by the dynamic acceleration component processing unit 153, and brush pressures PR corresponding to the respective differences DF. The data in the tables TB4 and TB5 is detected in advance through experimentation.

The motor 10 is in an unloaded state during the initialization process (S5) in FIG. 4, which is executed when the electric toothbrush 1 is turned on. In step S5, the differential vibration frequency detection unit 158 is inputted with a signal indicating the output voltage value of the rechargeable battery 13 from the voltage monitor 102.

The brush pressure searching unit 159 of the differential vibration frequency detection unit 158 searches the table TB4 based on the combination of the type of the operating mode specified by the user as inputted through the switch S and the voltage value indicated by the signal inputted from the voltage monitor 102. The vibration frequency DV corresponding to that combination of the voltage value and the operating mode is read out from the table TB4 based on the result of the search. The differential vibration frequency detection unit 158 stores the unloaded vibration frequency DV read out from the table TB4 in a predetermined region of the memory 121.

When the initialization process (step S5) ends, a brush pressure is produced due to brushing, and the torque of the motor 10 increases. The vibration frequency of the motor 10 detected by the dynamic acceleration component processing unit 153 also increases as a result.

In the brush pressure detection process (S50) carried out after the initialization process, the differential vibration frequency detection unit 158 detects (calculates) differences between the vibration frequencies detected sequentially by the dynamic acceleration component processing unit 153 and the vibration frequencies DV read out from the predetermined region of the memory 121. The brush pressure searching unit 159 then searches the table TB5 in the memory 121 based on the detected differences. The brush pressure PR corresponding to the difference DF that matches the detected difference is then read out from the table TB5 based on the result of the search. Through this, the brush pressure (brush pressure PR) is detected (estimated).

In this manner, the difference between the unloaded vibration frequency and the loaded vibration frequency that change in accordance with the output voltage (remaining charge) of the rechargeable battery 13 corresponds to the load, or in other words, the magnitude of the brush pressure, and thus the magnitude of the load, or in other words, the brush pressure, can be estimated based on the difference between the unloaded vibration frequency for the motor 10 and the vibration frequency when there is a load, as mentioned above.

Brush Pressure Communication

Figure 30:
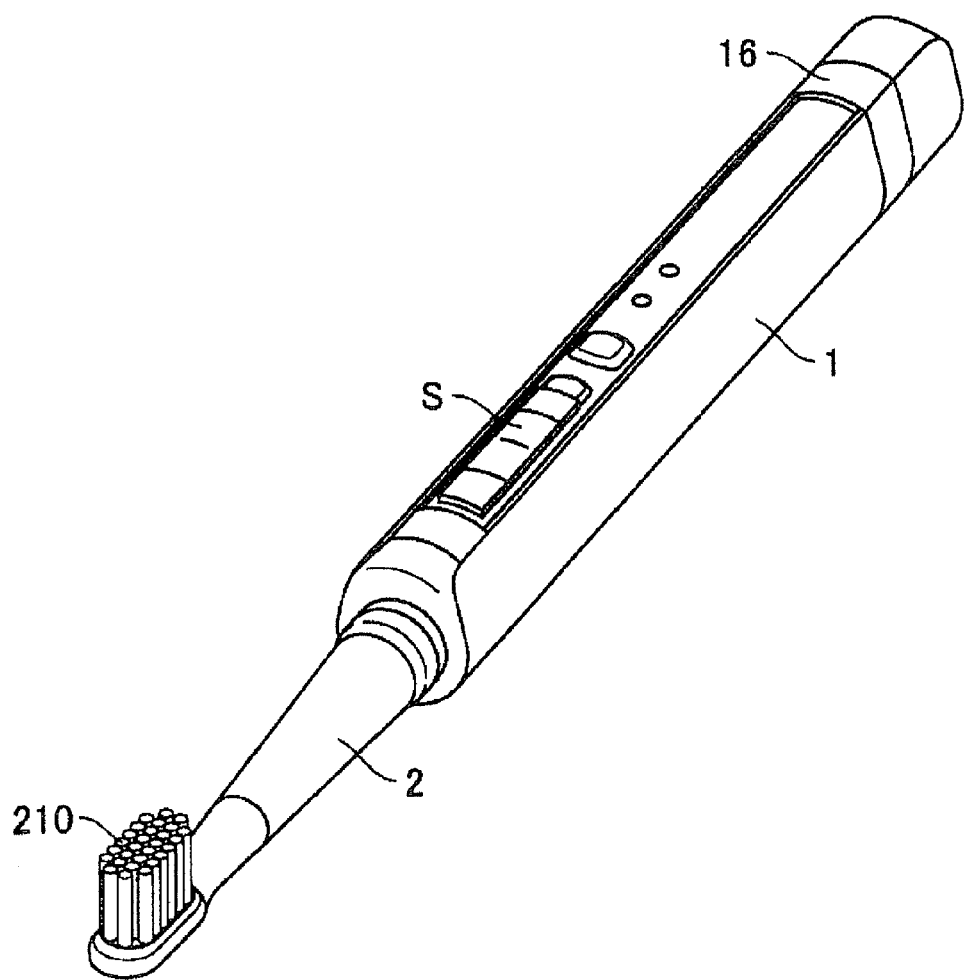
FIG. 30 is a diagram illustrating an example of the external appearance of an electric toothbrush.

FIG. 30 illustrates the external appearance of the electric toothbrush 1 into which the display unit 16 for communicating the detected brush pressure to the user is incorporated.

The brush pressure can be displayed in the display device 110 shown in FIG. 3 and in the display unit 16. The display unit 16 is configured of a light-emitting unit such as an LED (Light Emitting Diode), and is provided on an end of the main body 2 to be easily viewable by the user during brushing. The display unit 16 is disposed so as to wrap around the circumference of the housing of the approximately cylindrical main body 2. Disposing the display unit 16 on the end also makes it possible to check the display unit 16 in a mirror. Note that the display unit 16 may be provided on the end of the main body 2 located toward the bristles 210.

As a method for the display, the lighting state of the LED in the display unit 16 is changed in accordance with the detected brush pressure. For example, the LED is flashed at a higher speed the greater the brush pressure has been evaluated at, or the luminosity of the LED is increased. Alternatively, a red color may be emitted when the brush pressure is evaluated as being high, whereas a green color may be emitted when the brush pressure has been evaluated as being low.

The detected vibration frequency may be communicated by carrying out a display through the display device 110 or the display unit 16.

The method for communicating the brush pressure and the vibration frequency is not limited to using the display unit 16, and may be carried out by outputting audio, voice, or the like.

Note that the driving source need not be the DC motor 10. For example, a solenoid, a piezoelectric element, an ultrasonic vibrating element, or an actuator that employs an artificial muscle may be used as well.

In this manner, the embodiments and variations disclosed herein are to be understood in all ways as exemplary and in no ways limiting. The technical scope of the present invention is defined by the appended claims, and all variations that fall within the meaning and range of equivalency of the claims are intended to be embraced therein.

REFERENCE SIGNS LIST

1 electric toothbrush
15 accelerometer
16A, 16B pulse signal generation unit
17A operating mode input unit
18A, 18B duty ratio decision unit
19A battery voltage input unit
103 filter unit
120 CPU
120A, 120B PWM control unit
153 dynamic acceleration component processing unit
155 static acceleration component processing unit
156 consumed current detection unit
157 table searching unit
158 differential vibration frequency detection unit
159 brush pressure searching unit
1201, 1202 brush pressure estimation unit
TB1-TB5 table

The invention claimed is:

1. A toothbrush for performing care on an oral cavity using a vibrating member with bristles, the toothbrush comprising:
   a driving unit that includes a motor that vibrates the vibrating member;
   an accelerometer that outputs a signal having a waveform component representing a vibration frequency of the motor and an orientation signal representing an orientation of the vibration member;
   a vibration frequency detection unit that detects a vibration frequency of the vibration member based on the waveform component of the signal output by the accelerometer;
   a member pressure detecting unit that detects a degree of pressure acting on the vibration member based on the vibration frequency without using a detected current consumed by the motor such that, as the vibration frequency detected by the vibration frequency detection unit decreases, the pressure acting on the vibration member increases;
   a brushing area estimation unit that estimates a brushing area based on the orientation signal; and
   an output unit that outputs the degree of pressure in association with the estimated brushing area.

2. The toothbrush according to claim 1, wherein the member pressure detecting unit detects the degree of pressure based on a difference between the vibration frequency caused by rotation of the motor when the motor is unloaded and the vibration frequency detected by the vibration frequency detection unit.

3. The toothbrush according to claim 1, further comprising:
   a power source that supplies power to the toothbrush;
   a power detection unit that detects the power outputted by the power source; and
   a power compensation unit that supplements the power supplied to the driving unit based on a value of the power detected by the power detection unit.

4. The toothbrush according to claim 3, wherein the power compensation unit changes a duty ratio of a pulse signal supplied to the driving unit based on the value of the power detected by the power detection unit.

5. The toothbrush according to claim 1, wherein the detected degree of pressure is communicated.

6. The toothbrush according to claim 1, wherein the vibration frequency is displayed.

* * * * *